(12) United States Patent
Umezawa et al.

(10) Patent No.: US 12,110,507 B2
(45) Date of Patent: Oct. 8, 2024

(54) METHOD FOR PREPARING FUNCTIONAL HEPATIC PROGENITOR CELLS OR HEPATIC CELLS, OR FUNCTIONAL SMALL INTESTINAL EPITHELIAL PROGENITOR CELLS OR SMALL INTESTINAL EPITHELIAL CELLS

(71) Applicant: Akihiro Umezawa, Tokyo (JP)

(72) Inventors: Akihiro Umezawa, Tokyo (JP); Tohru Kiyono, Tokyo (JP)

(73) Assignee: Akihiro Umezawa, Tokyo (JP)

( * ) Notice: Subject to any disclaimer, the term of this patent is extended or adjusted under 35 U.S.C. 154(b) by 683 days.

(21) Appl. No.: 16/958,118

(22) PCT Filed: Dec. 27, 2018

(86) PCT No.: PCT/JP2018/048308
§ 371 (c)(1),
(2) Date: Jun. 25, 2020

(87) PCT Pub. No.: WO2019/131938
PCT Pub. Date: Jul. 4, 2019

(65) Prior Publication Data
US 2020/0339955 A1   Oct. 29, 2020

(30) Foreign Application Priority Data
Dec. 27, 2017   (JP) ................ 2017-251725

(51) Int. Cl.
*C12N 5/071* (2010.01)
*A61K 35/407* (2015.01)
*G01N 33/50* (2006.01)

(52) U.S. Cl.
CPC .......... *C12N 5/0672* (2013.01); *A61K 35/407* (2013.01); *G01N 33/5067* (2013.01);
(Continued)

(58) Field of Classification Search
CPC .............. C12N 5/0672; C12N 2500/05; C12N 2506/02; C12N 2506/45; C12N 2510/04;
(Continued)

(56) References Cited

U.S. PATENT DOCUMENTS

2010/0047853 A1* 2/2010 Kuo .................. C12N 5/0012
                                                    435/325
2015/0299289 A1* 10/2015 Urban ..................... C12N 7/00
                                                    435/320.1
(Continued)

FOREIGN PATENT DOCUMENTS

JP   2015535524   12/2015
WO   2011/016485   2/2011
(Continued)

OTHER PUBLICATIONS

Kondo, Yuki, et al. "An efficient method for differentiation of human induced pluripotent stem cells into hepatocyte-like cells retaining drug metabolizing activity." Drug Metabolism and Pharmacokinetics 29.3 (2014): 237-243.*

(Continued)

*Primary Examiner* — Jeremy C Flinders
*Assistant Examiner* — Thomas R. Amick
(74) *Attorney, Agent, or Firm* — Myers Bigel, P.A.

(57) ABSTRACT

Provided is a method for preparing functional hepatic (progenitor) cells or functional small intestinal epithelial (progenitor) cells, comprising the step of culturing an isolated cell population comprising hepatic (progenitor) cells or small intestinal epithelial (progenitor) cells in the presence of an antibiotic. Also, provided is a substantially homogeneous isolated cell population comprising functional hepatic progenitor cells, wherein an expression level of CYP3A4 in (Continued)

the functional hepatic progenitor cells is increased by at least 5 times the expression level thereof in a HepaRG® cell line.

11 Claims, 13 Drawing Sheets

Specification includes a Sequence Listing.

(52) U.S. Cl.
CPC ...... *C12N 2500/05* (2013.01); *C12N 2506/02* (2013.01); *C12N 2506/45* (2013.01); *C12N 2510/04* (2013.01)

(58) Field of Classification Search
CPC .......... C12N 2500/38; C12N 2501/105; C12N 2501/115; C12N 2510/00; C12N 2533/54; C12N 5/068; C12N 15/00; A61K 35/407; G01N 33/5067; A61L 27/38; A61P 1/16
See application file for complete search history.

(56) References Cited

U.S. PATENT DOCUMENTS

| 2016/0046904 A1 | 2/2016 | Mizuguchi et al. | |
| 2018/0147242 A1* | 5/2018 | Miyajima | ............ C12N 5/0671 |

FOREIGN PATENT DOCUMENTS

| WO | WO-2011016485 A1 * | 2/2011 | ............ C12N 5/067 |
| WO | 2014/168157 | 10/2014 | |
| WO | 2016/148216 | 9/2016 | |

OTHER PUBLICATIONS

Iwao, T., Toyota, M., Miyagawa, Y., Okita, H., Kiyokawa, N., Akutsu, H., . . . & Matsunaga, T. (2014). Differentiation of human induced pluripotent stem cells into functional enterocyte-like cells using a simple method. Drug metabolism and pharmacokinetics, 29(1), 44-51. (Year: 2014).*

Okita, K., Matsumura, Y., Sato, Y., Okada, A., Morizane, A., Okamoto, S., . . . & Yamanaka, S. (2011). A more efficient method to generate integration-free human iPS cells. Nature methods, 8(5), 409-412. (Year: 2011).*

Okita, K., Ichisaka, T., & Yamanaka, S. (2007). Generation of germline-competent induced pluripotent stem cells. nature, 448(7151), 313-317. (Year: 2007).*

Ghodsizadeh, A., Taei, A., Totonchi, M., Seifinejad, A., Gourabi, H., Pournasr, B., . . . & Baharvand, H. (2010). Generation of liver disease-specific induced pluripotent stem cells along with efficient differentiation to functional hepatocyte-like cells. Stem Cell Reviews and Reports, 6(4), 622-632. (Year: 2010).*

Boyd NL et al., Dissecting the role of human embryonic stem cell-derived mesenchymal cells in human umbilical vein endothelial cell network stabilization in three-dimensional environments. Tissue Eng Part A. Jan. 2013; 19(1-2):211-23 (Year: 2013).*

Aden et al Nature, vol. 282, Issue 5739, pp. 615-616 (1979) (Year: 1979).*

Sevrioukova (Sevrioukova, Irina F, and Thomas L Poulos. "Understanding the mechanism of cytochrome P450 3A4: recent advances and remaining problems." Dalton transactions (Cambridge, England : 2003) vol. 42,9 (2013): 3116-26.) (Year: 2003).*

Spinelli (Spinelli, Jessica B et al. "Metabolic recycling of ammonia via glutamate dehydrogenase supports breast cancer biomass." Science (New York, N.Y.) vol. 358,6365 (2017)). (Year: 2017).*

Chan, Christina et al. "Incompatibility of chemical protein synthesis inhibitors with accurate measurement of extended protein degradation rates." Pharmacology research & perspectives vol. 5,5 (2017)) (Year: 2017).*

International Search Report corresponding to International Application No. PCT/JP2018/048308 mailed Apr. 23, 2019.

Iwao et al. "Differentiation of Human Induced Pluripotent Stem Cells into Functional Enterocyte-like Cells Using a Simple Method", Drug Metab. Pharmacokinet. 29(1):44-51 (2014).

Kondo et al. "An Efficient Method for Differentiation of Human Induced Pluripotent Stem Cells into Hepatocyte-like Cells Retaining Drugs Metabolizing Activity", Drug Metab. Pharmacokinet. 29(3):237-243 (2014).

Inamura et al. "Efficient Generation of Hepatoblasts From Human ES cells and iPS Cells by Transient Overexpression of Homeobox Gene HEX", Molecular Therapy 19(2):400-407 (2011).

Iwadare "Effect of Drugs on Cultured Liver Cells II", Juntendo Medical Journal 26(1):29-42 (1980).

Nakamura et al. "Feeder-free and serum-free production of hepatocytes, cholangiocytes, and their proliferating progenitors from human pluripotent stem cells: application to liver-specific functional and cytotoxic assays", Cell Reprogram. 14(2):171-185 (2012).

Aninat et al. "Expression of Cytochromes P450, Conjugating Enzymes and Nuclear Receptors in Human Hepatoma HepaRG Cells", Drug Metabolism and Disposition 34(1):75-83 (2006).

Abe et al. "Endoderm-Specific Gene Expression in Embryonic Stem Cells Differentiated to Embryoid Bodies", Experimental Cell Research 229:27-34 (1996).

Soudais et al. "Targeted mutagenesis of the transcription factor GATA-4 gene in mouse embryonic stem cells disrupts visceral endoderm differentiation in vitro", Development 121:3877-3888 (1995).

* cited by examiner

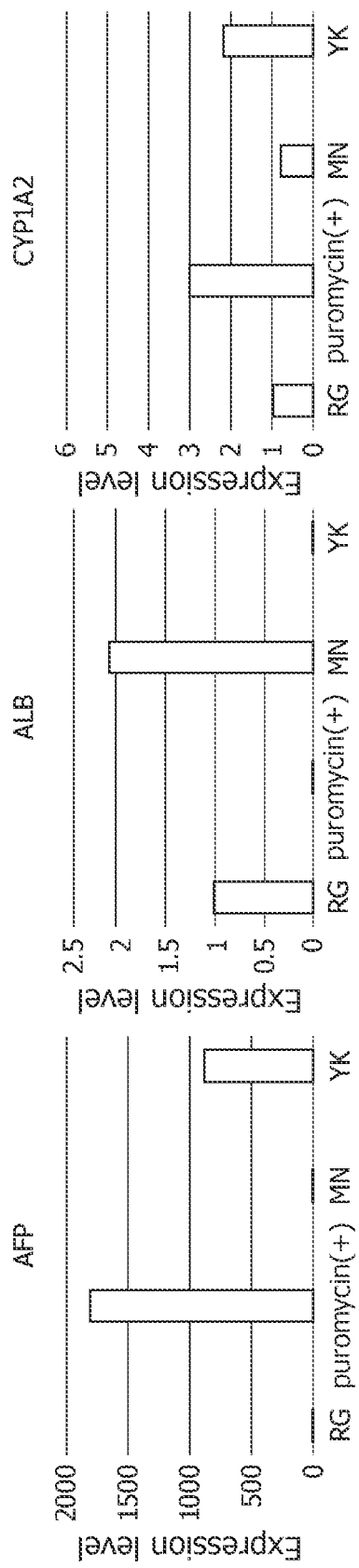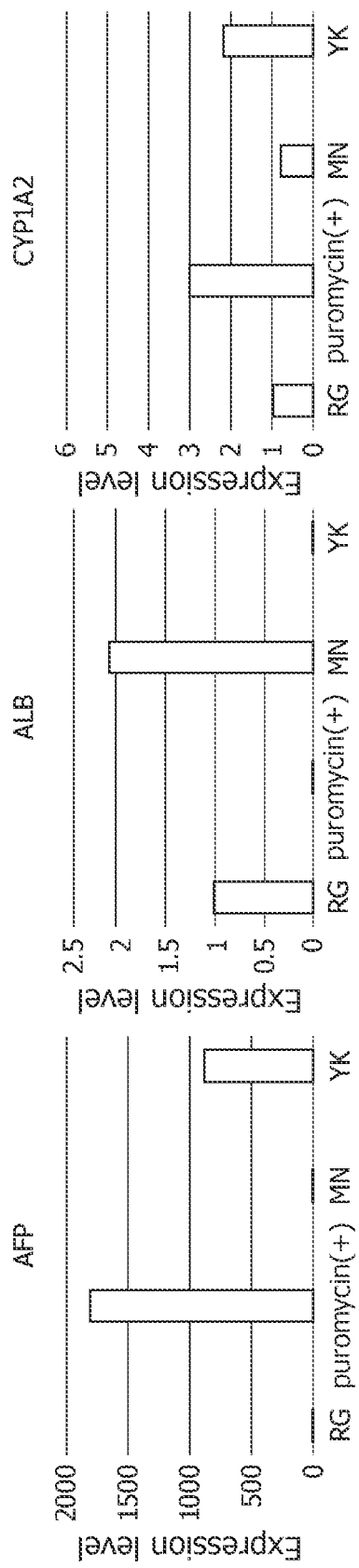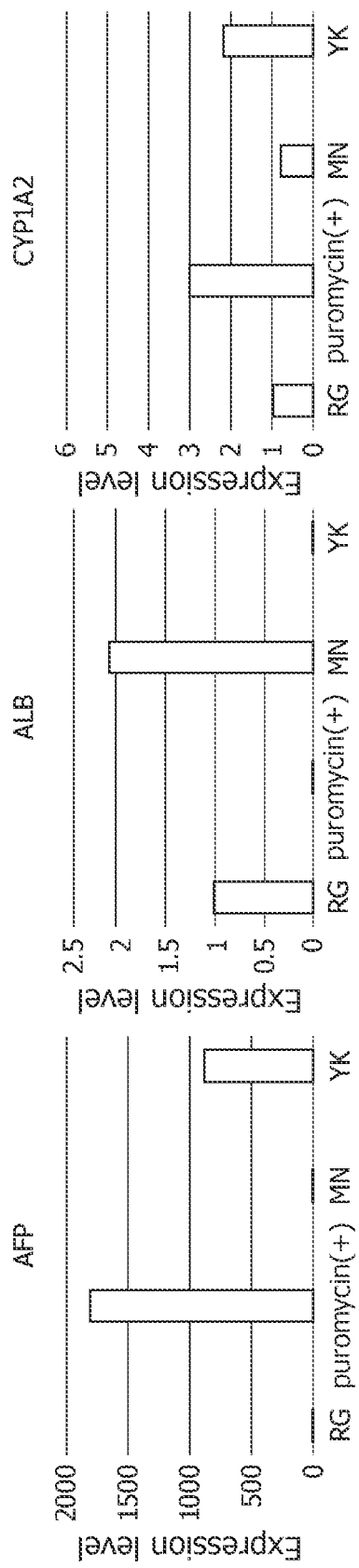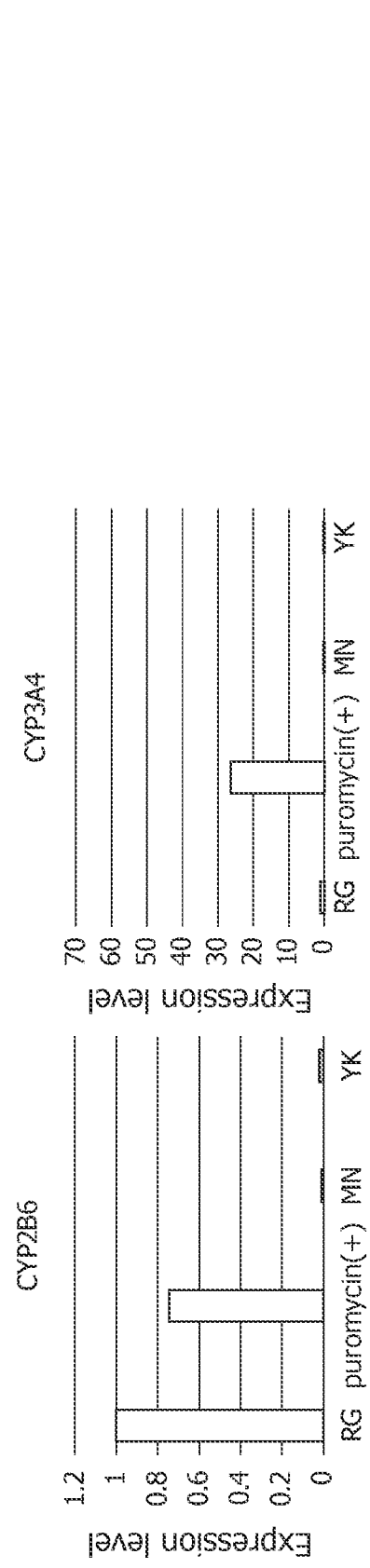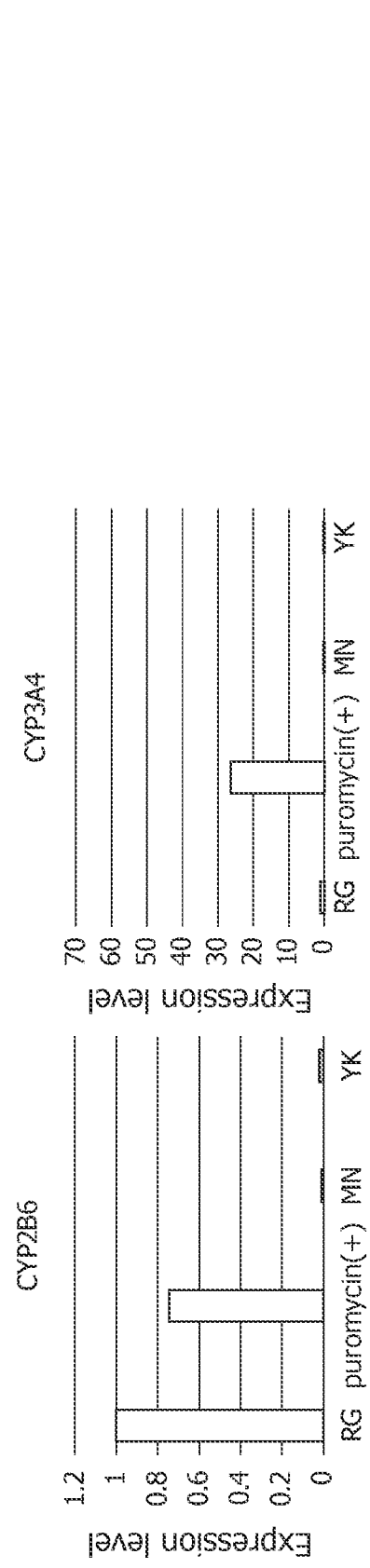

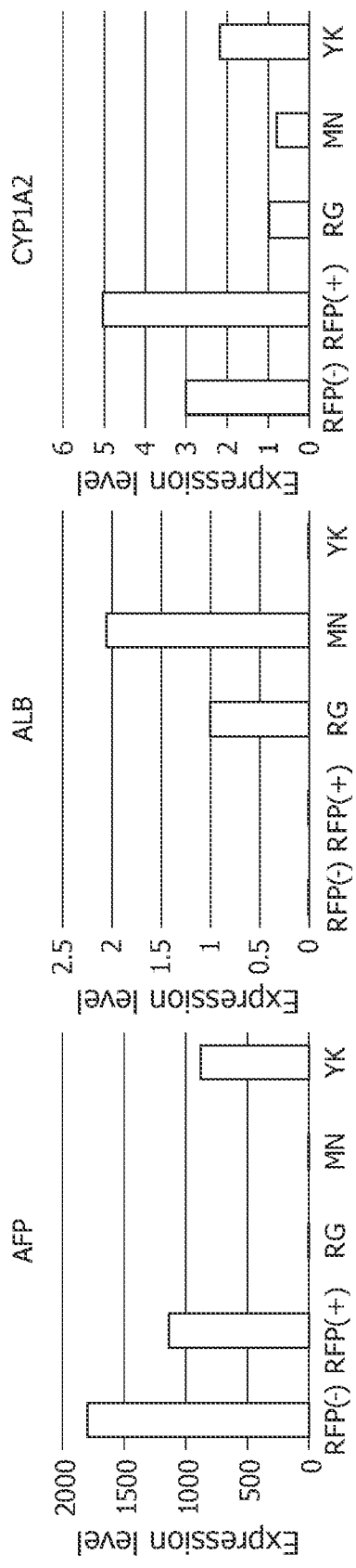
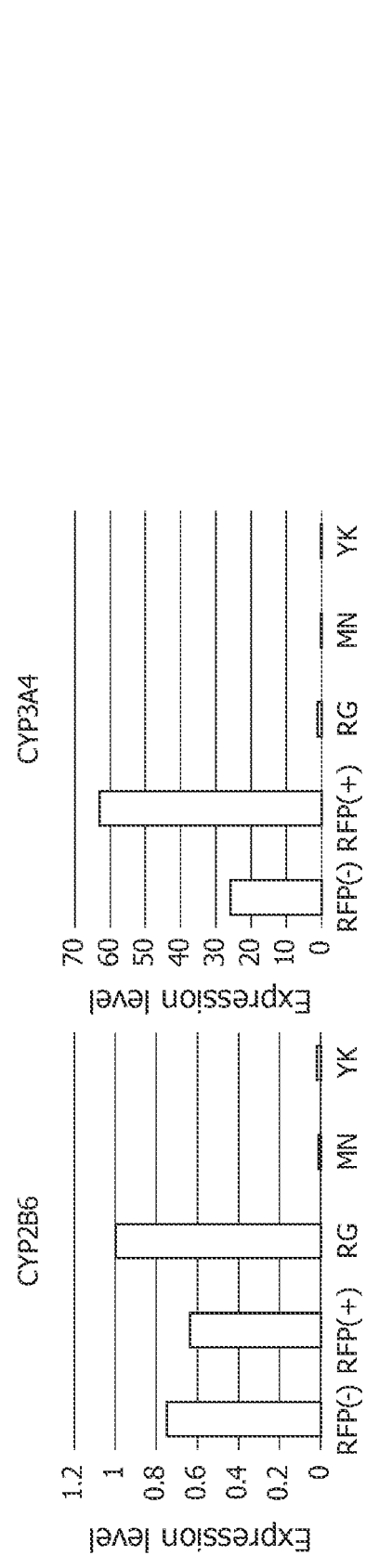

500μm

500μm

500μm

500μm

500μm

500μm

3000μm

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: AFP F-primer

<400> SEQUENCE: 1
agcttggtgg tggatgaaac                                               20

<210> SEQ ID NO 2
<211> LENGTH: 20
<212> TYPE: DNA
<213> ORGANISM: Artificial Sequence
<220> FEATURE:

<223> OTHER INFORMATION: AFP R-primer

<400> SEQUENCE: 2
ccctcttcag caaagcagac                                                    20

<210> SEQ ID NO 3
<211> LENGTH: 20
<212> TYPE: DNA
<213> ORGANISM: Artificial Sequence
<220> FEATURE:
<223> OTHER INFORMATION: ALB F-primer

<400> SEQUENCE: 3
tggcacaatg aagtgggtaa                                                    20

<210> SEQ ID NO 4
<211> LENGTH: 20
<212> TYPE: DNA
<213> ORGANISM: Artificial Sequence
<220> FEATURE:
<223> OTHER INFORMATION: ALB R-primer

<400> SEQUENCE: 4
ctgagcaaag gcaatcaaca                                                    20

<210> SEQ ID NO 5
<211> LENGTH: 20
<212> TYPE: DNA
<213> ORGANISM: Artificial Sequence
<220> FEATURE:
<223> OTHER INFORMATION: CYP1A2 F-primer

<400> SEQUENCE: 5
caatcaggtg gtggtgtcag                                                    20

<210> SEQ ID NO 6
<211> LENGTH: 20
<212> TYPE: DNA
<213> ORGANISM: Artificial Sequence
<220> FEATURE:
<223> OTHER INFORMATION: CYP1A2 R-primer

<400> SEQUENCE: 6
gctcctggac tgttttctgc                                                    20

<210> SEQ ID NO 7
<211> LENGTH: 20
<212> TYPE: DNA
<213> ORGANISM: Artificial Sequence
<220> FEATURE:
<223> OTHER INFORMATION: CYP2B6 F-primer

<400> SEQUENCE: 7
tcctttctga ggttccgaga                                                    20

<210> SEQ ID NO 8
<211> LENGTH: 20
<212> TYPE: DNA
<213> ORGANISM: Artificial Sequence
<220> FEATURE:
<223> OTHER INFORMATION: CYP2B6 R-primer

<400> SEQUENCE: 8
tcccgaagtc cctcatagtg                                                    20

```
<210> SEQ ID NO 9
<211> LENGTH: 20
<212> TYPE: DNA
<213> ORGANISM: Artificial Sequence
<220> FEATURE:
<223> OTHER INFORMATION: CYP3A4 F-primer

<400> SEQUENCE: 9
caagacccct ttgtggaaaa                                                     20

<210> SEQ ID NO 10
<211> LENGTH: 20
<212> TYPE: DNA
<213> ORGANISM: Artificial Sequence
<220> FEATURE:
<223> OTHER INFORMATION: CYP3A4 R-primer

<400> SEQUENCE: 10
cgaggcgact ttctttcatc                                                     20

<210> SEQ ID NO 11
<211> LENGTH: 20
<212> TYPE: DNA
<213> ORGANISM: Artificial Sequence
<220> FEATURE:
<223> OTHER INFORMATION: UBI F-primer

<400> SEQUENCE: 11
ggagccgagt gacaccattg                                                     20

<210> SEQ ID NO 12
<211> LENGTH: 21
<212> TYPE: DNA
<213> ORGANISM: Artificial Sequence
<220> FEATURE:
<223> OTHER INFORMATION: UBI R-primer

<400> SEQUENCE: 12
cagggtacga ccatcttcca g                                                   21

<210> SEQ ID NO 13
<211> LENGTH: 20
<212> TYPE: DNA
<213> ORGANISM: Artificial Sequence
<220> FEATURE:
<223> OTHER INFORMATION: CPS1 F-primer

<400> SEQUENCE: 13
caagttttgc agtggaatcg                                                     20

<210> SEQ ID NO 14
<211> LENGTH: 20
<212> TYPE: DNA
<213> ORGANISM: Artificial Sequence
<220> FEATURE:
<223> OTHER INFORMATION: CPS1 R-primer

<400> SEQUENCE: 14
ggacagatgc ctgagcctaa                                                     20

<210> SEQ ID NO 15
<211> LENGTH: 23
<212> TYPE: DNA
<213> ORGANISM: Artificial Sequence
<220> FEATURE:
<223> OTHER INFORMATION: OCT F-primer
```

```
-continued

<400> SEQUENCE: 15
tttccaaggt taccaggtta caa                                      23

<210> SEQ ID NO 16
<211> LENGTH: 21
<212> TYPE: DNA
<213> ORGANISM: Artificial Sequence
<220> FEATURE:
<223> OTHER INFORMATION: OCT R-primer

<400> SEQUENCE: 16
ctgggcaagc agtgtaaaaa t                                        21
```

METHOD FOR PREPARING FUNCTIONAL HEPATIC PROGENITOR CELLS OR HEPATIC CELLS, OR FUNCTIONAL SMALL INTESTINAL EPITHELIAL PROGENITOR CELLS OR SMALL INTESTINAL EPITHELIAL CELLS

RELATED APPLICATIONS

This application is a 35 U.S.C. § 371 national phase application of PCT Application PCT/JP2018/048308 filed Dec. 27, 2018, which claims priority to Japanese Application No. 2017-251725 filed Dec. 27, 2017. The entire contents of each are incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 5576-372 ST25.txt, 3,421 bytes in size, generated on Jun. 24, 2020, and filed via EFS-Web, is provided in lieu of a paper copy. This Sequence Listing is hereby incorporated by reference into the specification for its disclosures.

FIELD OF THE INVENTION

The present invention relates to a method for preparing functional hepatic progenitor cells or hepatic cells, or functional small intestinal epithelial progenitor cells or small intestinal epithelial cells, and functional hepatic progenitor cells or hepatic cells, or functional small intestinal epithelial progenitor cells or small intestinal epithelial cells obtained thereby, and regenerative medicine or drug toxicity evaluation using the cells.

BACKGROUND OF THE INVENTION

Heretofore, liver transplantation has been practiced in causal therapy for liver diseases such as liver cirrhosis and is still a mainstream treatment method today. However, there are numerous problems, such as organ donor shortage, high costs, and histocompatibility, for the wide use of liver transplantation in general medicine. Hence, the establishment of liver regenerative medicine methods using hepatic cells or hepatic progenitor cells is an urgent need.

In the field of drug discovery research, laboratory animals are frequently used in toxicity tests of drugs. However, in vivo pharmacokinetics may differ depending on the species differences between humans and animals. Thus, tests using laboratory animals may fail to sufficiently evaluate the safety of drugs and lead to discontinuation of drug development due to hepatotoxicity reported at a clinical trial stage. Hence, the establishment of in vitro drug toxicity evaluation systems using human hepatic cells is strongly desired for predicting in vivo pharmacokinetics in humans at the initial stage of drug discovery research.

A plurality of human hepatic cell lines have been established so far. However, most of these cell lines have very low drug metabolizing activity and lack sufficient liver functions. HepaRG® cells (Non-Patent Document 1) maintain liver functions, but are not suitable for use in liver regenerative medicine because this cell line is derived from liver cancer and is tumorigenic. Moreover, since the cell line is derived from one particular individual, difference in drug metabolism and toxicity among individuals cannot be evaluated using the cell line. On the other hand, human primary cultured hepatic cells are limited, in the first place, by the obtainment of the human liver serving as a starting material. In addition, these cells are very difficult to supply stably because the cells lose their drug metabolizing activity through subculture and can thus maintain liver functions only for a very short period. A further problem of the cells is very large difference among lots.

Thus, approaches of inducing ES cells or iPS cells to differentiate into functional hepatic cells have received attention in recent years. A plurality of methods for inducing differentiation have previously been reported (Non-Patent Documents 2 and 3). However, all the previously reported methods for inducing differentiation have low differentiation efficiency and fail to prepare hepatic cells having sufficient liver functions with high yields and high reproducibility. Thus, methods that can highly efficiently and stably prepare hepatic cells having sufficient ability to metabolize drugs, and functional hepatic cells obtained by such methods are still necessary.

Also, small intestinal epithelial cells are known to express drug transporters and drug metabolizing enzymes and to play an important role in drug metabolism, as in hepatic cells. In particular, functional small intestinal epithelial cells are necessary for predicting the bioavailability of oral preparations and evaluating their safety. However, methods that can highly efficiently and stably prepare small intestinal epithelial cells having sufficient ability to metabolize drugs, and functional small intestinal epithelial cells obtained by such methods, have not yet been established.

CITATION LIST

Non-Patent Document

[Non-Patent Document 1] Aninat, C. et al., Drug Metab. Dispos., 2006; 34 (1): 75-83
[Non-Patent Document 2] Soudais, C. et al., Development, 1995; 121 (11): 3877-88
[Non-Patent Document 3] Abe, K. et al., Exp Cell Res., 1996; 229 (1): 27-34

SUMMARY OF INVENTION

Technical Problem

An object of the present invention is to solve problems in the conventional techniques and to provide a method for highly efficiently and stably preparing functional hepatic progenitor cells or hepatic cells, or functional small intestinal epithelial progenitor cells or small intestinal epithelial cells having sufficient ability to metabolize drugs.

Solution to Problem

The present inventors have earnestly researched, and as a result, found that hepatic (progenitor) cells or small intestinal epithelial (progenitor) cells having sufficient ability to metabolize drugs can be prepared by culturing a cell population comprising hepatic (progenitor) cells or small intestinal epithelial (progenitor) cells in the presence of an antibiotic.

Specifically, according to one embodiment, the present invention provides a method for preparing functional hepatic progenitor cells or functional hepatic cells, or functional small intestinal epithelial progenitor cells or functional small intestinal epithelial cells, the method comprising the step of culturing an isolated cell population comprising hepatic progenitor cells or hepatic cells, or small intestinal epithelial progenitor cells or small intestinal epithelial cells in the presence of an antibiotic.

The isolated cell population is preferably a primary culture derived from a hepatic tissue or a small intestinal epithelial tissue.

The isolated cell population is preferably differentiated from stem cells.

The stem cells are preferably embryonic stem (ES) cells.

The stem cells are preferably induced pluripotent stem (iPS) cells.

The iPS cells are preferably derived from a healthy individual.

The iPS cells are preferably derived from a drug-induced liver injury patient or a drug-induced small intestinal injury patient.

The antibiotic is preferably selected from the group consisting of puromycin, blasticidin S, G418, hygromycin, phleomycin and phleomycin D1.

The antibiotic is preferably 0.1 to 100 μg/ml puromycin.

The culture step is preferably performed in the presence of a hepatic differentiation inducing factor.

The hepatic differentiation inducing factor is preferably selected from the group consisting of a cytokine, a cell growth factor, a ROCK inhibitor, a MAPK inhibitor, an ALK inhibitor and an extracellular matrix.

The method preferably further comprises the step of culturing the isolated cell population in the presence of ammonia.

According to one embodiment, the present invention also provides functional hepatic progenitor cells or hepatic cells, or functional small intestinal epithelial progenitor cells or small intestinal epithelial cells obtained by the method.

According to one embodiment, the present invention also provides a substantially homogeneous isolated cell population comprising functional hepatic progenitor cells, wherein an expression level of CYP3A4 in the functional hepatic progenitor cells is increased by at least 5 times the expression level thereof in a HepaRG® cell line.

The functional hepatic progenitor cells preferably express at least one member selected from the group consisting of α-fetoprotein, albumin, CYP1A2 and CYP2B6 at a higher level than that of the HepaRG® cell line.

The functional hepatic progenitor cells are preferably CD44-positive and/or EpCAM-positive.

The substantially homogeneous isolated cell population is preferably immortalized.

According to one embodiment, the present invention also provides functional hepatic progenitor cells deposited under deposition No. BP-02591 and/or BP-02592 with National Institute of Technology and Evaluation (NITE) Patent Microorganisms Depositary.

According to one embodiment, the present invention also provides a method for treating a subject having hepatic dysfunction, the method comprising the step of administering the substantially homogeneous isolated cell population to the subject.

According to one embodiment, the present invention also provides a pharmaceutical composition for treating hepatic dysfunction, comprising the substantially homogeneous isolated cell population.

According to one embodiment, the present invention also provides a method for evaluating the toxicity of a test compound, comprising the steps of: (1) contacting functional hepatic cells differentiated from the substantially homogeneous isolated cell population or the deposited functional hepatic progenitor cells with the test compound; and (2) analyzing a degree of injury to the functional hepatic cells.

Advantageous Effects of Invention

According to the method according to the present invention, functional hepatic (progenitor) cells or functional small intestinal epithelial (progenitor) cells having sufficient ability to metabolize drugs can be prepared easily and inexpensively with high reproducibility by merely culturing an isolated cell population comprising hepatic (progenitor) cells or small intestinal epithelial (progenitor) cells in the presence of an antibiotic. Also, functional hepatic (progenitor) cells or functional small intestinal epithelial (progenitor) cells obtained by the method according to the present invention are useful for regenerative medicine or drug toxicity evaluation.

BRIEF DESCRIPTION OF DRAWINGS

FIGS. 7a-7e are graphs showing results of a qRT-PCR analysis to investigate the expression of hepatic cell markers in hepatic cells differentiated from HepaSM cells (puromycin (+)), HepaRG® cells (RG), immortalized mature hepatic cells (MN), and hepatic cells obtained by inducing the differentiation without selection based on puromycin (YK).

FIGS. 8a-8e are graphs showing results of a qRT-PCR analysis to investigate the expression hepatic cell markers when hepatic cells differentiated from HepaSM cells were or were not treated with rifampicin.

DESCRIPTION OF EMBODIMENTS

Figure 1:
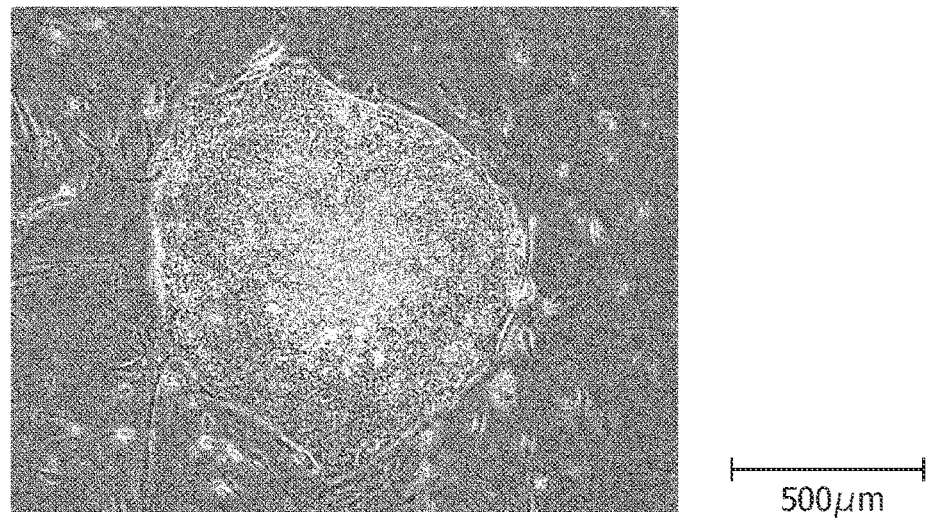
FIG. 1 is a diagram showing a phase-contrast micrograph of fulminant hepatitis patient-derived iPS cells (iPSC-K cells).

Hereinafter, the present invention will be described in detail. However, the present invention is not limited by the embodiments described in the present specification.

According to the first embodiment, the present invention provides a method for preparing functional hepatic progenitor cells or functional hepatic cells, or functional small intestinal epithelial progenitor cells or functional small intestinal epithelial cells, the method comprising the step of culturing an isolated cell population comprising hepatic progenitor cells or hepatic cells, or small intestinal epithelial progenitor cells or small intestinal epithelial cells in the presence of an antibiotic.

In the present embodiment, the "functional hepatic progenitor cells" mean cells having the ability to differentiate into hepatic cells having the same or similar ability to metabolize drugs as that of hepatic cells in the living body. In the present embodiment, the "functional hepatic cells" means hepatic cells having the same or similar ability to metabolize drugs as that of hepatic cells in the living body. In the present embodiment, the "functional small intestinal epithelial progenitor cells" mean cells having the ability to differentiate into small intestinal epithelial cells having the same or similar ability to metabolize drugs as that of small intestinal epithelial cells in the living body. In the present embodiment, the "functional small intestinal epithelial cells" mean small intestinal epithelial cells having the same or similar ability to metabolize drugs as that of small intestinal epithelial cells in the living body. In this context, the phrase "having the ability to metabolize drugs" for cells mean that the cells express a drug metabolizing enzyme cytochrome P450, specifically, at least one cytochrome P450 selected from the group consisting of CYP3A4, CYP1A2 and CYP2B6, in an amount sufficient for exhibiting drug metabolizing activity. The "hepatic cells" can include both mature hepatic cells and immature hepatic cells.

In the present embodiment, the "isolated cell population" means a population consisting of a plurality of cells isolated from an in vivo environment (e.g., a tissue) and cultured in vitro.

The isolated cell population according to the present embodiment can be a primary culture derived from a hepatic tissue or a small intestinal epithelial tissue. The hepatic tissue or the small intestinal epithelial tissue that can be used in the present embodiment may be derived from a freely chosen vertebrate and is preferably derived from a mammal such as a mouse, a rat, a rabbit, sheep, a pig, cattle, a goat, a monkey, or a human, particularly preferably derived from a human. The hepatic tissue or the small intestinal epithelial tissue may be either a fetal tissue or an adult tissue. A method for preparing the primary culture from the hepatic tissue has been sufficiently established, and the primary culture from the hepatic tissue can be prepared according to a method known in the art (Cole, K. E. et al., Cancer Res., 1986; 46 (3):1290-6; and Adams R. S. et al., Proc. Natl. Acad. Sci. USA., 1992; 89 (19): 8981-5). The primary culture from the small intestinal epithelial tissue can also be prepared according to a method known in the art (Wang et al., Nature, 2015; 522: 173-178).

The isolated cell population according to the present embodiment can be differentiated from stem cells. In the present embodiment, the "stem cells" mean cells having the ability to self-renew and the ability to differentiate. The stem cells are classified, according to their ability to differentiate, into pluripotent stem cells, multipotent stem cells, unipotent stem cells, and the like. Any of stem cells can be used in the method of the present embodiment as long as the stem cells that can be used in the present embodiment has the ability to differentiate into at least hepatic cells or small intestinal epithelial cells. Even stem cells that originally differentiate into fat cells, skeletal muscle cells, osteoblasts, or the like and differentiate into neither hepatic cells nor small intestinal epithelial cells can be used in the method of the present embodiment as long as the stem cells are capable of acquiring the ability to differentiate into hepatic cells or small intestinal epithelial cells by procedures of differentiation as mentioned later.

The stem cells that can be used in the method of the present embodiment can be derived from a freely chosen vertebrate and is preferably derived from a mammal such as a mouse, a rat, a rabbit, sheep, a pig, cattle, a goat, a monkey, or a human, particularly preferably derived from a human. The stem cells that can be used in the present embodiment may be prepared from blastocyst, a fetal tissue, an adult tissue or umbilical cord blood. The tissue for preparing the stem cells is not particularly limited, and the stem cells can be prepared from, for example, bone marrow, muscle, the brain, the pancreas, the liver, or the kidney. The stem cells that can be used in the present embodiment can be embryonic stem (ES) cells, somatic stem cells, or induced pluripotent stem (iPS) cells and are preferably ES cells or iPS cells. The iPS cells may be derived from a healthy individual or may be derived from a drug-induced liver injury patient or a drug-induced small intestinal injury patient.

A method for preparing the ES cells and the iPS cells has been sufficiently established, and these cells can be prepared according to a method known in the art (Takahashi, K. et al., Cell 2007; 131 (5): 861-72, doi:10.1016/j.cell.2007.11.019). Alternatively, an already established ES cell line or iPS cell line may be obtained from, for example, RIKEN BRC or ATCC (American Type Culture Collection).

Various culture conditions for inducing the stem cells to differentiate into hepatic (progenitor) cells or small intestinal epithelial (progenitor) cells are known. The isolated cell population comprising hepatic (progenitor) cells or small intestinal epithelial (progenitor) cells having the desired degree of differentiation or maturity can be prepared by appropriately selecting the conditions. The stem cells can be differentiated into hepatic (progenitor) cells or small intestinal epithelial (progenitor) cells, for example, by forming embryoid bodies from the stem cells. Culture conditions for forming the embryoid bodies have been sufficiently established, and the embryoid bodies can be formed, for example, by suspension-culturing the stem cells for 1 day to 2 weeks in a medium containing no differentiation inhibiting factor. Alternatively, the stem cells can be differentiated (induced to differentiate) into hepatic (progenitor) cells, for example, by culturing the stem cells in a differentiation induction medium supplemented with a liquid factor such as activin A, FGF, or BMP. Also, the stem cells can be differentiated (induced to differentiate) into small intestinal epithelial (progenitor) cells, for example, by culturing the stem cells in a differentiation induction medium supplemented with a liquid factor such as heregulin β1, IGF, or bFGF. Without the use of the liquid factor, the stem cells may be placed on a base material with a patterned cell adhesion region and non-cell-adhesion region and thereby differentiated into gut organoid (JP 2017-184749 A).

A kit for inducing the stem cells to differentiate into hepatic (progenitor) cells is commercially available, and such a commercially available product may be used. Preferred examples of the commercially available product include Cellartis® iPS Cell to Hepatocyte Differentiation System (Cellartis, Y30055).

In the method of the present embodiment, an isolated cell population comprising hepatic progenitor cells or hepatic cells, or small intestinal epithelial progenitor cells or small intestinal epithelial cells is cultured in the presence of an antibiotic. In this context, in the present embodiment, the "antibiotic" means a general cytotoxic compound that inhibits the survival and proliferation of cells. In the method of the present embodiment, the isolated cell population comprising hepatic progenitor cells or hepatic cells, or small intestinal epithelial progenitor cells or small intestinal epithelial cells is cultured in the presence of an antibiotic so that cells that cannot metabolize the antibiotic are killed while only functional hepatic progenitor cells or functional hepatic cells, or functional small intestinal epithelial progenitor cells or functional small intestinal epithelial cells, which can metabolize the antibiotic, can be selected.

Any antibiotic other than a cell wall synthesis inhibitor can be used as the antibiotic according to the present embodiment. For example, a cell membrane function inhibitor, a protein synthesis inhibitor, a nucleic acid synthesis inhibitor, or a folic acid synthesis inhibitor can be used. One antibiotic selected therefrom can be used alone, or two or more thereof can be used in combination. Preferably, an antibiotic that is generally used for selecting a stable transformant carrying an exogenous gene (so-called antibiotic for selection) can be used as the antibiotic according to the present embodiment. Examples of the antibiotic for selection include, but are not limited to, puromycin, blasticidin S, G418 (also known as Geneticin™), hygromycin, and bleomycin family-derived antibiotics such as bleomycin, phleomycin, and phleomycin D1 (also known as Zeocin™). The antibiotic that can be used in the method of the present embodiment is preferably puromycin.

In the method of the present embodiment, the isolated cell population comprising hepatic progenitor cells or hepatic cells, or small intestinal epithelial progenitor cells or small intestinal epithelial cells is cultured for a certain period in a medium supplemented with the antibiotic. The concentration of the antibiotic differs depending on the type of the cells and/or the type of the antibiotic and can be in the range of, for example, 0.1 to 5000 µg/ml. The culture period differs depending on the type of the antibiotic, and the culture can be performed, for example, over 1 to 10 days. In the case of using, for example, puromycin, as the antibiotic, culture for 1 to 10 days at an antibiotic concentration of 0.1 to 100 µg/ml is preferred, and culture for 1 to 5 days at an antibiotic concentration of 0.5 to 50 µg/ml is particularly preferred. For example, a concentration of 20 to 100 µg/ml of phleomycin for use as the antibiotic, a concentration of 20 to 2000 µg/ml of hygromycin used, a concentration of 1 to 100 µg/ml of blasticidin S used, a concentration of 20 to 2000 µg/ml of phleomycin D1 used, or a concentration of 50 to 5000 µg/ml of G418 used is preferred in culture for 1 to 10 days.

Examples of the medium that can be used in the method of the present embodiment include basal media such as DMEM and RPMI1640. One medium selected therefrom can be used alone, or two or more types thereof can be used as a mixture. In the method of the present embodiment, the isolated cell population comprising hepatic progenitor cells or hepatic cells, or small intestinal epithelial progenitor cells or small intestinal epithelial cells is preferably placed in a concentration range of $1 \times 10^6$ to $1 \times 10^8$ cells/ml.

For preparing the functional hepatic progenitor cells or the functional hepatic cells by the method of the present embodiment, it is preferred to appropriately add a hepatic differentiation inducing factor to the medium. One member selected from the group consisting of a cytokine, a cell growth factor, a ROCK inhibitor, a MAPK inhibitor, an ALK inhibitor and an extracellular matrix can be used alone as the hepatic differentiation inducing factor, or two or more thereof can be used in combination. For example, oncostatin M (approximately 2 to 200 ng/ml), hepatocyte growth factor (HGF) (approximately 5 to 500 ng/ml), Wnt (approximately 10 to 1000 ng/ml), epithelial cell growth factor (EGF) (approximately 10 to 1000 ng/ml), R-spondin 1 (approximately 10 to 1000 ng/ml), insulin-transferrin-sodium selenite (ITS) (approximately 50 to 5000 ng/ml), nicotinamide (approximately 1 to 100 mM), or hydrocortisone (approximately 40 to 4000 ng/ml) can be used as the cytokine and the cell growth factor, though the cytokine and the cell growth factor are not limited thereto. For example, Y-27632 (approximately 1 to 100 µmol/ml) can be used as the ROCK inhibitor. For example, SB202190 (approximately 0.5 to 50 µM) can be used as the MAPK inhibitor. For example, A81-01 (approximately 10 to 1000 ng/ml) can be used as the ALK inhibitor.

In the case of preparing the functional small intestinal epithelial progenitor cells or the functional small intestinal epithelial cells by the method of the present embodiment, it is preferred to appropriately add a small intestinal epithelial differentiation inducing factor to the medium. One member selected from the group consisting of a cytokine, a cell growth factor, a ROCK inhibitor, a MAPK inhibitor, an ALK inhibitor and an extracellular matrix can be used alone as the small intestinal epithelial differentiation inducing factor, or two or more thereof can be used in combination. For example, oncostatin M (approximately 2 to 200 ng/ml), Wnt (approximately 10 to 1000 ng/ml), epithelial cell growth factor (EGF) (approximately 10 to 1000 ng/ml), R-spondin 1 (approximately 10 to 1000 ng/ml), insulin-transferrin-sodium selenite (ITS) (approximately 50 to 5000 ng/ml), nicotinamide (approximately 1 to 100 mM), or hydrocortisone (approximately 40 to 4000 ng/ml) can be used as the cytokine and the cell growth factor, though the cytokine and the cell growth factor are not limited thereto. For example, Y-27632 (approximately 1 to 100 µmol/ml) can be used as the ROCK inhibitor. For example, SB202190 (approximately 0.5 to 50 µM) can be used as the MAPK inhibitor. For example, A81-01 (approximately 10 to 1000 ng/ml) can be used as the ALK inhibitor.

The culture in the method of the present embodiment may be performed by an adhesion culture method or may be performed by a suspension culture method and is preferably performed by an adhesion culture method. The adhesion culture can preferably employ a plate or the like coated with an extracellular matrix such as laminin, collagen, gelatin, fibronectin, or Matrigel, or with feeder cells such as mouse embryonic fibroblasts (MEFs). The culture conditions in the method of the present embodiment can be appropriately set depending on the type of the stem cells used. For example, mammal-derived stem cells are preferably cultured under conditions of 37° C. and 5% $CO_2$.

The method of the present embodiment may further comprise the step of culturing the isolated cell population comprising hepatic progenitor cells or hepatic cells, or small intestinal epithelial progenitor cells or small intestinal epithelial cells in the presence of ammonia. Specifically, the isolated cell population comprising hepatic progenitor cells or hepatic cells, or small intestinal epithelial progenitor cells or small intestinal epithelial cells can be cultured for a certain period in a medium supplemented with antibiotic. The concentration of ammonia can be in the range of, for example, 5 to 15 mg/ml. The culture period can be, for example, over 1 to 10 days, preferably over 1 to 5 days.

In the method of the present embodiment, the step of culturing an isolated cell population comprising hepatic progenitor cells or hepatic cells, or small intestinal epithelial progenitor cells or small intestinal epithelial cells in the presence of an antibiotic, and the step of culturing the isolated cell population in the presence of ammonia can be performed sequentially or simultaneously. For example, the isolated cell population may be cultured for a certain period in the presence of an antibiotic and then, after replacement of the medium with a medium supplemented with ammonia, cultured for a certain period; the isolated cell population may be cultured for a certain period in the presence of ammonia and then, after replacement of the medium with a medium supplemented with the antibiotic, cultured for a certain period; or the isolated cell population may be cultured for a certain period in a medium supplemented with both the antibiotic and ammonia.

According to the method of the present embodiment, functional hepatic cells or functional small intestinal epithelial cells, or their progenitor cells having sufficient ability to metabolize drugs can be prepared by merely culturing an isolated cell population comprising hepatic progenitor cells or hepatic cells, or small intestinal epithelial progenitor cells or small intestinal epithelial cells in the presence of an antibiotic.

According to the second embodiment, the present invention provides functional hepatic progenitor cells or functional hepatic cells, or functional small intestinal epithelial progenitor cells or functional small intestinal epithelial cells obtained by the method disclosed above.

The "functional hepatic progenitor cells", the "functional hepatic cells", the "functional small intestinal epithelial progenitor cells" and the "functional small intestinal epithelial cells" according to the present embodiment are as defined in the first embodiment. Thus, whether the cells obtained by the above method are functional hepatic progenitor cells or functional hepatic cells, or functional small intestinal epithelial progenitor cells or functional small intestinal epithelial cells can be confirmed based on the expression of at least one cytochrome P450 selected from the group consisting of CYP3A4, CYP1A2 and CYP2B6 and can be particularly preferably confirmed based on significant expression of CYP3A4.

According to the third embodiment, the present invention provides a substantially homogeneous isolated cell population comprising functional hepatic progenitor cells, wherein an expression level of CYP3A4 in the functional hepatic progenitor cells is increased by at least 5 times the expression level thereof in a HepaRG® cell line.

The "functional hepatic progenitor cells" and the "isolated cell population" according to the present embodiment are as defined in the first embodiment.

In the present embodiment, the phrase "substantially homogeneous" for the isolated cell population means that the isolated cell population is in a state comprising the cells of interest at a proportion of at least 90%. Thus, the isolated cell population of the present embodiment comprises the functional hepatic progenitor cells at a proportion of at least 90%, preferably 95% or more, particularly preferably 99% or more. Hereinafter, the substantially homogeneous isolated cell population comprising functional hepatic progenitor cells is referred to as a "functional hepatic progenitor cell population" in the present specification.

Whether the hepatic progenitor cells included in the functional hepatic progenitor cell population of the present embodiment are functional hepatic progenitor cells can be determined on the basis of significant expression of CYP3A4. The expression level of CYP3A4 in the functional hepatic progenitor cell population of the present embodiment is increased by at least 5 times, preferably 20 or more times, particularly preferably 100 or more times the expression level thereof in a HepaRG® cell line. The expression levels of CYP3A4 and markers described below can be quantitatively analyzed by a known approach such as quantitative RT-PCR or Western blot.

The functional hepatic progenitor cells in the functional hepatic progenitor cell population of the present embodiment preferably express, in addition to CYP3A4, at least one member selected from the group consisting of a hepatic progenitor cell/immature hepatic cell marker α-fetoprotein, an immature hepatic cell/mature hepatic cell marker albumin, CYP1A2 and CYP2B6 at a higher level than that of the HepaRG® cell line. In addition, the functional hepatic progenitor cells in the functional hepatic progenitor cell population of the present embodiment preferably express ornithine transcarbamylase (OTC), an enzyme constituting the urea circuit which metabolizes ammonia, and/or carbamyl phosphate synthetase 1 (CPS1) at a higher level than that of the HepaRG® cell line. More preferably, the functional hepatic progenitor cells comprised in the functional hepatic progenitor cell population of the present embodiment can be further positive to any one or both of hepatic progenitor cell/immature hepatic cell markers CD44 and EpCAM (CD326).

The functional hepatic progenitor cell population of the present embodiment can be prepared by the method according to the first embodiment. In order to further increase the proportion of the functional hepatic progenitor cells comprised in the functional hepatic progenitor cell population of the present embodiment, cells expressing a cell surface marker for hepatic progenitor cells/immature hepatic cells may be separated from a cell population obtained by the method according to the first embodiment. Preferred examples of the cell surface marker for hepatic progenitor cells/immature hepatic cells include CD44, EpCAM (CD326), carboxypeptidase M (CPM), CD133, and CD13. The separation of the marker-positive cells can be performed by a known approach such as fluorescence activated cell sorting (FACS) or magnetic cell separation (MACS).

The functional hepatic progenitor cell population of the present embodiment may be optionally immortalized. In this context, the term "immortalized" for cells means that the cells maintain a state capable of proliferating even after repetition of a certain number of divisions, i.e., the cells have infinite proliferative capacity. A method for immortalizing cells has already been established, and a known approach can be adopted. The cells can be immortalized, for example, by transferring an immortalizing gene such as telomerase reverse transcriptase (TERT) gene to the cells through a retrovirus vector.

The functional hepatic progenitor cells thus obtained were designated as HepaSM and HepaNS and deposited under deposition Nos. BP-02591 and BP-02592 with an international depository authority National Institute of Technology and Evaluation (NITE) Patent Microorganisms Depositary (formerly International Patent Organism Depositary of the National Institute of Advanced Industrial Science and Technology) (deposition date: Dec. 6, 2017, receipt No. AP-02591 and AP-02592).

The functional hepatic progenitor cells and the functional hepatic cells according to the second embodiment, and the functional hepatic progenitor cell population according to the third embodiment are useful in the treatment of liver diseases or in drug metabolism toxicity tests.

According to the fourth embodiment, the present invention provides a method for treating a subject having hepatic dysfunction, the method comprising the step of administering the functional hepatic progenitor cell population to the subject.

In the present embodiment, the "treating" includes not only full cure of hepatic dysfunction in the subject but remission of symptoms of hepatic dysfunction, alleviation of conditions of hepatic dysfunction, or delay or arrest of progression of the pathological condition.

The "subject" according to the present embodiment can be a freely chosen vertebrate and is preferably a mammal such as a mouse, a rat, a rabbit, sheep, a pig, cattle, a goat, a monkey, or a human, particularly preferably a human. The subject can be of a freely chosen age, including infant, child, young, adult and aged subjects.

Examples of the "hepatic dysfunction" according to the present embodiment include, but are not limited to, hepatitis, liver cirrhosis, liver cancer, inborn error of metabolism, acute liver failure (fulminant hepatitis), and chronic liver failure.

The method of the present embodiment can be performed by administering the functional hepatic progenitor cell population to the subject having hepatic dysfunction. In this context, the functional hepatic progenitor cell population to be administered can be allogeneic, isogeneic or self-derived to the subject. In the present embodiment, the functional hepatic progenitor cell population may be genetically modified. For example, a normal gene corresponding to an abnormal gene causative of the disease can be transferred to a functional hepatic progenitor cell population differentiated from iPS cells prepared from a patient with inborn error of metabolism, and the resulting functional hepatic progenitor cell population can be administered to the patient.

In the present embodiment, the functional hepatic progenitor cell population can be administered by an appropriate method, for example, injection, implantation, or transplantation. Preferably, the functional hepatic progenitor cell population can be injected into the portal vein of the subject. In the case of the injection of the functional hepatic progenitor cell population into the portal vein, a cell suspension ($1 \times 10^6$ cells/ml) prepared using, for example, phosphate buffered saline, can be injected into the portal vein at a rate of approximately 2 ml/min. In this context, the dose of the functional hepatic progenitor cell population can differ depending on the age and body weight of the subject, the severity of hepatic dysfunction, etc. and can be, for example, $1 \times 10^5$ to $1 \times 10^{10}$ cells/kg (body weight), preferably $1 \times 10^6$ to $1 \times 10^8$ cells/kg (body weight). The dose may be administered in one portion or may be administered in a plurality of portions.

According to the fifth embodiment, the present invention provides a pharmaceutical composition for treating hepatic dysfunction, comprising the functional hepatic progenitor cell population.

The "hepatic dysfunction" and the "treating" according to the present embodiment are as defined in the fourth embodiment.

The pharmaceutical composition of the present embodiment contains the functional hepatic progenitor cell population as an active ingredient. The pharmaceutical composition of the present embodiment may consist of the active ingredient or may further comprise optional components such as a known pharmaceutically acceptable carrier, a buffer, and other components (e.g., a hepatocyte growth factor). The pharmaceutical composition of the present embodiment can be prepared, for example, as an injection dosage form, using a carrier, such as phosphate buffered saline, which can maintain the survival of the cells serving as the active ingredient. The administration method and dose of the pharmaceutical composition of the present embodiment can be as described in the fourth embodiment.

The method according to the fourth embodiment and the pharmaceutical composition according to the fifth embodiment are useful in the causal treatment of hepatic dysfunction.

According to the sixth embodiment, the present invention provides a method for evaluating the toxicity of a test compound, comprising the steps of: (1) contacting functional hepatic cells differentiated from the functional hepatic progenitor cell population or the deposited functional hepatic progenitor cells with the test compound; and (2) analyzing a degree of injury to the functional hepatic cells.

The toxicity evaluation method of the present embodiment employs functional hepatic cells differentiated from the functional hepatic progenitor cell population or the deposited functional hepatic progenitor cells. Culture conditions for inducing the hepatic progenitor cells to differentiate into hepatic cells are known as described in the first embodiment, and functional hepatic cells having the desired degree of differentiation or maturity can be obtained under appropriate culture conditions.

In the toxicity evaluation method of the present embodiment, the test compound is contacted with the functional hepatic cells. Examples of the test compound include, but are not particularly limited to, synthetic compounds such as drugs, and natural compounds such as cell extracts. These test compounds may be novel or may be known.

The contact between the functional hepatic cells and the test compound can be performed, for example, by adding the test compound to a culture medium for the functional hepatic cells or a buffer solution such as phosphate buffered saline or a Tris-HCl buffer solution and incubating therein the cells for a certain time. The concentration of the test compound to be added differs depending on the type of the compound and can be appropriately selected within the range of, for example, 20 nM to 500 µM. The incubation time can be preferably 24 to 48 hours.

Subsequently, the degree of injury to the functional hepatic cells is analyzed. The degree of injury to the functional hepatic cells can be analyzed, for example, by measuring the survival rate of the functional hepatic cells or the amount of a liver injury marker such as aspartate transaminase (AST) emigrating from the cells. When the survival rate of the cells is significantly decreased as compared with before the contact with the test compound or when the amount of the liver injury marker emigrating from the cells is significantly increased as compared with before this contact, the test compound can be evaluated as having hepatotoxicity and not being promising as a drug. On the other hand, when the survival rate of the cells is equivalent to or higher than that before the contact with the test compound or when the amount of the liver injury marker emigrating from the cells is equivalent to or less than that before this contact, the test compound can be evaluated as having no hepatotoxicity and being promising as a drug.

The method of the present embodiment is useful in screening for a candidate compound of a drug.

Examples

Hereinafter, the present invention will be further described with reference to Examples. However, these Examples do not limit the present invention by any means.

<1. Preparation of iPS Cells Derived from Fulminant Hepatitis Patients> iPS cells were prepared from fibroblasts of a fulminant hepatitis patient by the following procedures; the skin obtained by biopsy from the fulminant hepatitis patient (male, 7 months old) was cultured to obtain fibroblasts. To the obtained fibroblasts, human genes of Oct3/4, Sox2, Klf4 and c-Myc were transferred using a Sendai virus vector. Then, the cells were cultured for 2 weeks to confirm the appearance of a dome-like colony. The colony thus appearing was isolated, transferred onto MEF feeder cells, and subcultured in hiPSC medium (having the composition described below).

Table 1. Composition of hiPSC Medium

TABLE 1

| KnockOut DMEM | Thermo Fisher Scientific | 10829-018 | 380 ml |
|---|---|---|---|
| Knockout SR | Thermo Fisher Scientific | 10828-028 | 100 ml |
| GlutaMAX | Gibco | 35050-061 | 5 ml |
| Pen Strep | Gibco | 15140-122 | 5 ml |
| MEM NEAA | Gibco | 11140-050 | 5 ml |
| Sodium Pyruvate | Gibco | 11360-070 | 5 ml |
| 2-Mercaptoethanol | Gibco | 21985-023 | 500 µl |
| bFGF | Invitrogen | PHG0023 | 500 µl |

The results are shown in FIG. 1. The formation of a flat colony with a clear contour by subculture was confirmed, as in human ES cells or already established iPS cells, showing that iPS cells derived from the fulminant hepatitis patient were obtained. Hereinafter, the iPS cells are referred to as "iPSC-K cells".

iPS cells were also prepared from fibroblasts of another fulminant hepatitis patient by the same procedures as described above. Hereinafter, the iPS cells are referred to as "iPSC-O cells".

<2. Preparation of Functional Hepatic Progenitor Cells>
(2-1. Formation of Embryoid Bodies (EBs))

The iPSC-K cells were cultured until becoming approximately 80% confluent. The medium was removed, and the cells were washed with PBS. Then, StemPro Accutase (Thermo Fisher Scientific Inc.) was added thereto, and the cells were incubated under conditions of 37° C., and 5% $CO_2$ for 10 to 20 minutes. The colony was dissociated by gentle tapping of the dish and then suspended by the addition of hiPSC medium. The obtained cell suspension was transferred to a dish coated with gelatin, and incubated under conditions of 15 minutes, 37° C., and 5% $CO_2$ to remove the feeder cells. The supernatant was centrifuged, and the recovered iPSC-K cells were suspended in EB medium (having the composition described below). The iPSC-K cells were placed at a concentration of $1\times10^6$ cells/well in a 96-well plate for suspension culture (Thermo Fisher Scientific Inc., 174929) and cultured for 10 days under conditions of 37° C. and 5% $CO_2$ to form embryoid bodies (hereinafter, referred to as "EBs").

Table 2. Composition of EB Medium

TABLE 2

| KnockOut DMEM | Thermo Fisher Scientific | 10829-018 | 380 ml |
|---|---|---|---|
| Knockout SR | Thermo Fisher Scientific | 10828-028 | 100 ml |
| GlutaMAX | Gibco | 35050-061 | 5 ml |
| Pen Strep | Gibco | 15140-122 | 5 ml |
| MEM NEAA | Gibco | 11140-050 | 5 ml |
| Sodium Pyruvate | Gibco | 11360-070 | 5 ml |
| 2-Mercaptoethanol | Gibco | 21985-023 | 250 µl |

(2-2. Induction of EBs to Differentiate into Functional Hepatic Progenitor Cells)

The EBs were recovered and suspended in XF32 medium (Uchida, H. et al., JCI Insight, 2017; 2 (1): e86492, doi: 10.1172/jci.insight.86492). The EBs were placed at a concentration of 20 EBs/well in a 24-well plate coated with collagen, and differentiated into hepatic progenitor cells by adhesion culture at 37° C. for 35 days in 5% $CO_2$. Then, the cells were further cultured for 2 days using modified SCM-6F8 medium (Wang, X. et al., Nature, 2015; 522 (7555): 173-8, doi:10.1038/nature14484, Epub 2015 Jun. 3) supplemented with 3 µg/ml puromycin (Wako Pure Chemical Industries, Ltd., #160-23151).

Table 3. Composition of XF32 Medium

TABLE 3

| KnockOut DMEM | Thermo Fisher Scientific | 10829-018 | 405 ml | |
|---|---|---|---|---|
| CTS KnockOut SR XenoFree | Thermo Fisher Scientific | 10828-013 | 75 ml | |
| GlutaMAX | Gibco | 35050-061 | 5 ml | |
| Pen Strep | Gibco | 15140-122 | 5 ml | |
| MEM NEAA | Gibco | 11140-050 | 5 ml | |
| Sodium Pyruvate | Gibco | 11360-070 | 5 ml | |
| bFGF | Invitrogen | PHG0023 | 1 ml | (10 ng/ml) |
| IGF | Sigma | I1271 | 100 µl | (10 µg/100 µl) |
| Heleglin β | Wako | 080-09001 | 50 µl | (5 µg/50 µl) |
| L-ascorvic acid | Sigma | A4544 | 500 µl | (50 µg/ml) |

Figure 2A:
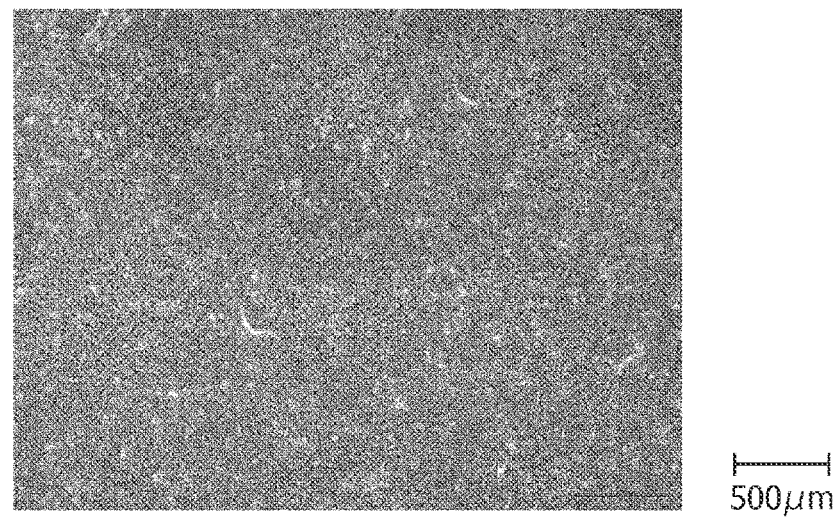
FIGS. 2a-2b are diagrams showing phase-contrast micrographs (a) before puromycin treatment and (b) after puromycin treatment as to hepatic progenitor cells differentiated from iPSC-K cells.
Figure 2B:
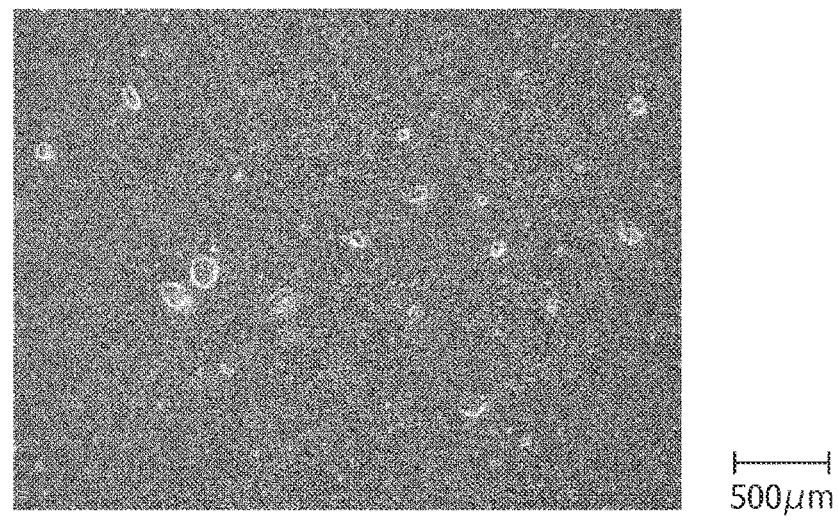

The results are shown in FIGS. 2a-2b. Cells obtained by the adhesion culture of EBs (FIG. 2(a)) were cultured in the presence of puromycin to obtain a colony of the cells (FIG. 2(b)). Functional hepatic progenitor cells obtained by the growth culture of this colony selected with puromycin were designated as "HepaNS" and deposited under deposition No. BP-02592 with an international depositary authority National Institute of Technology and Evaluation (NITE) Patent Microorganisms Depositary (deposition date: Dec. 6, 2017, receipt No. AP-02592).

(2-3. Immortalization of Functional Hepatic Progenitor Cells)

Subsequently, the functional hepatic progenitor cells thus obtained were immortalized by the transfer of human telomerase reverse transcriptase (TERT) gene, mutant human CDK4 (CDK4R24C) gene, and human cyclin D1 gene. The transfer of these genes was performed according to the procedures described in PLoS One, 2012; 7 (1): e29677, doi:10.1371/journal.pone.0029677, Epub 2012 Jan. 19 using lentivirus vectors CSII-CMV-hTERT, CSII-TRE-Tight-hCDK4R24C, and CSII-TRE-Tight-cyclin D1. The obtained immortalized functional hepatic progenitor cells were designated as "HepaSM" and deposited under deposition No. BP-02591 with an international depository authority National Institute of Technology and Evaluation (NITE) Patent Microorganisms Depositary (deposition date: Dec. 6, 2017, receipt No. AP-02591).

The HepaSM cells were cultured for 7 days under conditions of 37° C. and 5% $CO_2$ using modified SCM-6F8 medium and thereby induced to differentiate into hepatic cells. The obtained hepatic cells were analyzed as described below.

<3. Analysis of Hepatic Cells Differentiated from Functional Hepatic Progenitor Cells>

The cells differentiated from the HepaSM cells were subjected to hematoxylin-eosin staining and immunostaining with hepatic cell markers. The immunostaining with hepatic cell markers was performed by the following procedures: the medium was removed, and a 4% paraformaldehyde solution was added to the cells, which were then fixed at 4° C. for 10 minutes. After removal of the solution, a 0.1% Triton-X (Nacalai Tesque, Inc.) solution was added to the cells, which were then permeabilized at room temperature for 10 minutes. After removal of the solution, Protein Block Serum-Free Ready-to-use (Dako, X0909) was added thereto, followed by blocking treatment at room temperature for 30 minutes. An anti-CYP3A4 antibody (C-17) (Santa Cruz Biotechnology, Inc., sc-27639) (diluted 1/1000), an anti-albumin antibody (Cedarlane, CLFAG2140) (diluted 1/50), or an anti-α-fetoprotein (AFP) antibody (R&D Systems, Inc., MAB1368) (diluted 1/100) was used as a primary antibody and reacted with the cells overnight at 4° C. Rabbit anti-Goat IgG (H+L) Cross-Adsorbed Secondary Antibody, Alexa Fluor 488 (Thermo Fisher Scientific Inc., A11078), GFP Tag Polyclonal Antibody, Alexa Fluor 488 (Thermo Fisher Scientific Inc., A21311), or Goat anti-Mouse IgG1 Cross-Adsorbed Secondary Antibody, Alexa Fluor 546 (Thermo Fisher Scientific Inc., A21123) (all diluted 1/1000) was used as a secondary antibody and reacted with the cells at room temperature for 30 minutes.

Figure 3:
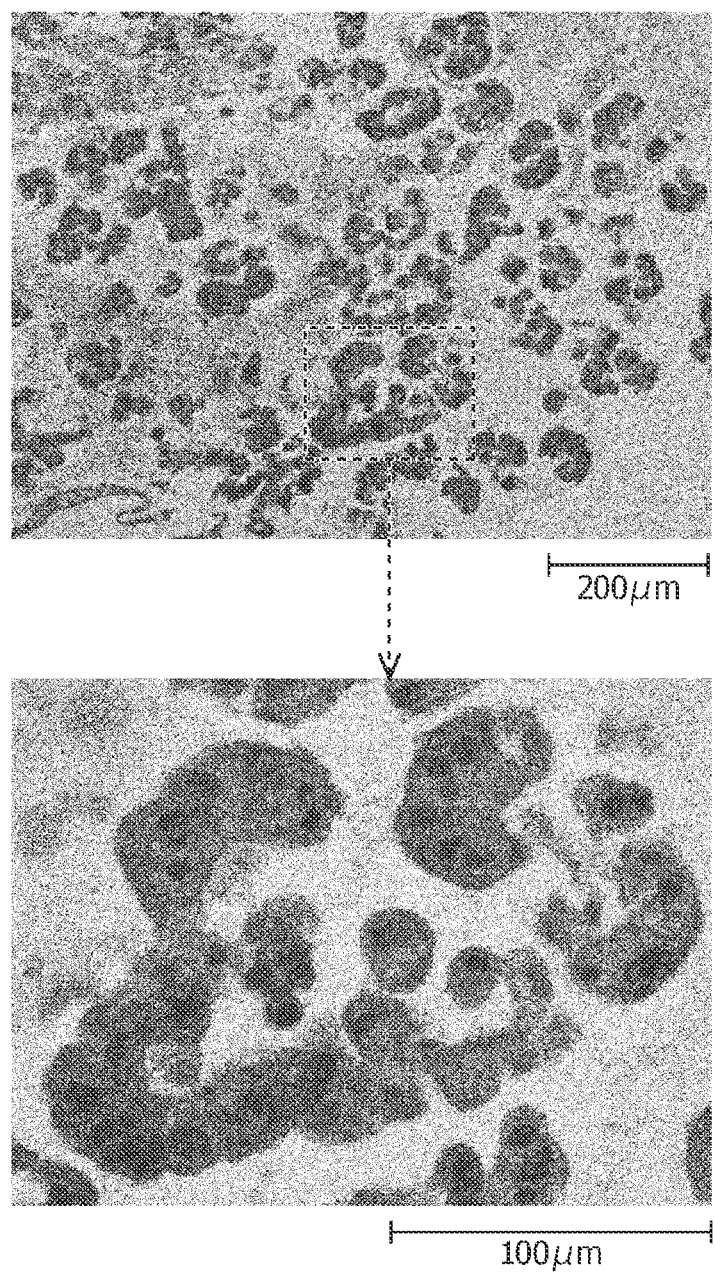
FIG. 3 is a diagram showing micrographs (hematoxylin-eosin staining) of cells differentiated from HepaSM cells.
Figure 4:
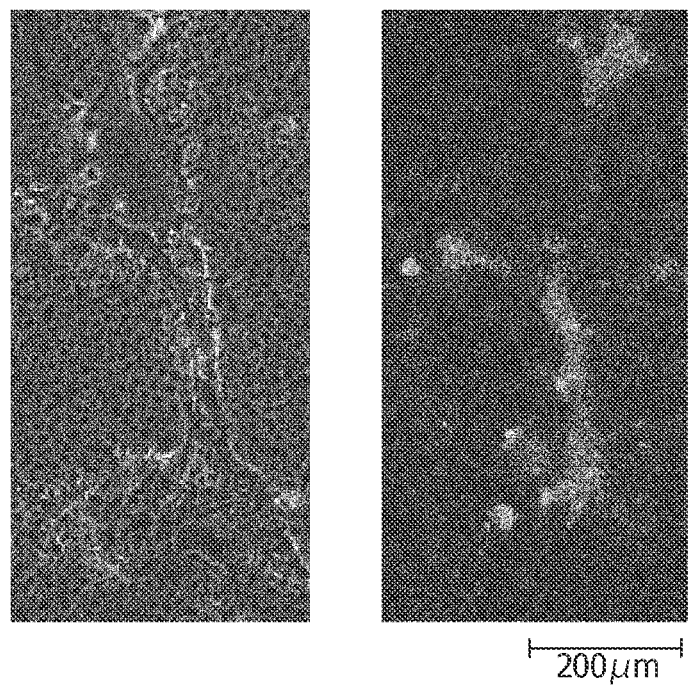
FIG. 4 is a diagram showing micrographs (right: bright field, left: immunostaining (CYP3A4)) of cells differentiated from HepaSM cells.
Figure 5:
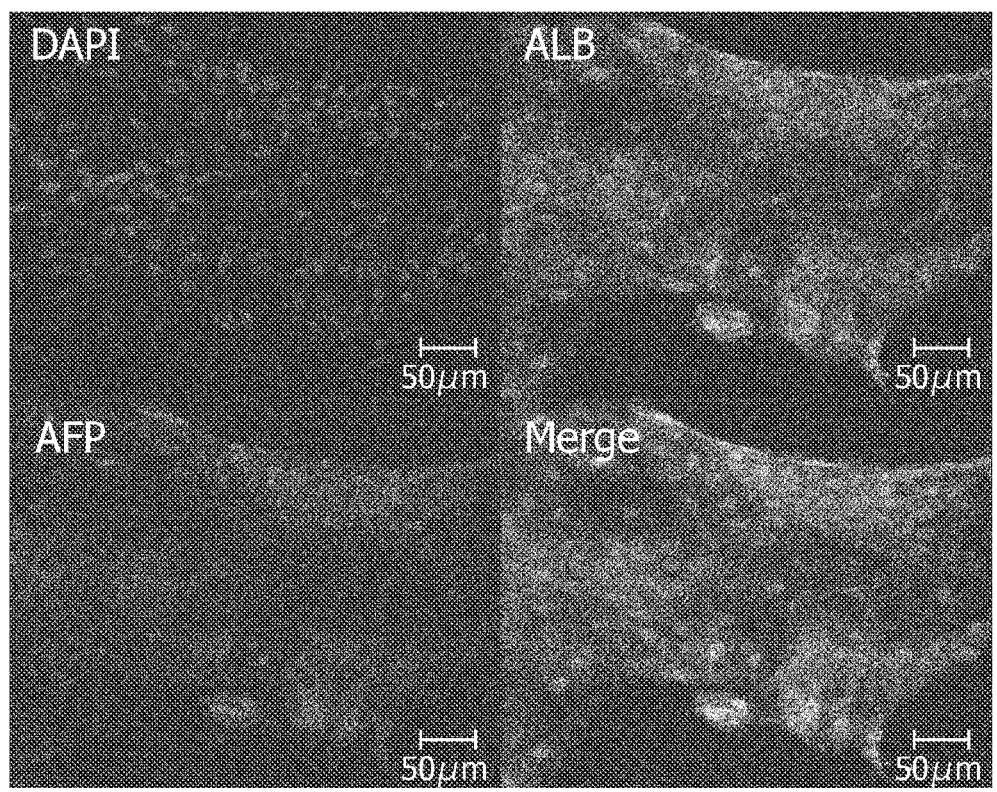
FIG. 5 is a diagram showing a fluorescence micrograph in which the expression of hepatic cell markers in cells differentiated from HepaSM cells was confirmed by immunocytochemistry.

The results are shown in FIGS. 3 to 5. As a result of hematoxylin-eosin staining, the cells differentiated from the HepaSM cells were confirmed to exhibit the morphology of hepatic cells (FIG. 3). As a result of immunostaining, the cells differentiated from the HepaSM cells were confirmed to express hepatic cell markers CYP3A4, albumin (ALB) and α-fetoprotein (AFP) (FIGS. 4 and 5). These results showed that the HepaSM cells are hepatic progenitor cells.

Subsequently, the expression levels of CYP3A4, albumin and α-fetoprotein in the hepatic cells differentiated from the HepaSM cells were analyzed by quantitative RT-PCR (qRT-PCR). Total RNA was extracted from the hepatic cells differentiated from the HepaSM cells using RNeasy Micro Kit (Qiagen N.V., 74004) according to the protocol included in the kit. 1 μg of the total RNA was reverse-transcribed using SuperScript III First-Strand Synthesis System for RT-PCR (Thermo Fisher Scientific Inc.) according to the protocol included in the kit to prepare cDNA. The obtained cDNA was preserved at −20° C.

qRT-PCR was performed with the obtained cDNA as a template using the primer set described below. The qRT-PCR reaction was performed using Platinum SYBR Green qPCR SuperMix-UDG (Thermo Fisher Scientific Inc.) according to the protocol included in the kit. The PCR reaction conditions were as follows: 50° C. for 2 minutes×1 cycle, 95° C. for 2 minutes×1 cycle, (95° C. for 15 seconds and 60° C. for 30 seconds)×40 cycles, 95° C. for 15 seconds×1 cycle, 60° C. for 15 seconds×1 cycle, 95° C. for 15 seconds×1 cycle, and 50° C. for 2 minutes×1 cycle. Measurement was performed using Quant Studio 12K Flex (Applied Biosystems). The Ct value of each gene was calculated by automatic analysis using analytical software installed in the apparatus, and corrected with the expression level of internal standard ubiquitin gene. Undifferentiated iPSC-K cells subcultured over an equivalent period without induction of differentiation and selection in the presence of puromycin were used as a control.

Table 4. Primer Set (1) Used in qRT-PCR

TABLE 4

| Gene | Forward and Reverse primers(5'→3') | SEQ NO. |
| --- | --- | --- |
| AFP | AGCTTGGTGGTGGATGAAAC | 1 |
|  | CCCTCTTCAGCAAAGCAGAC | 2 |
| ALB | TGGCACAATGAAGTGGGTAA | 3 |
|  | CTGAGCAAAGGCAATCAACA | 4 |
| CYP1A2 | CAATCAGGIGGTGGTGTCAG | 5 |
|  | GCTCCTGGACTGTTTTCTGC | 6 |
| CYP2B6 | TCCTTTCTGAGGTTCCGAGA | 7 |
|  | TCCCGAAGTCCCTCATAGTG | 8 |
| CYP3A4 | CAAGACCCCTTTGTGGAAAA | 9 |
|  | CGAGGCGACTTTCTTTCATC | 10 |
| UBIQUITIN | GGAGCCGAGTGACACCATTG | 11 |
|  | CAGGGTACGACCATCTTCCAG | 12 |

Figure 6A:
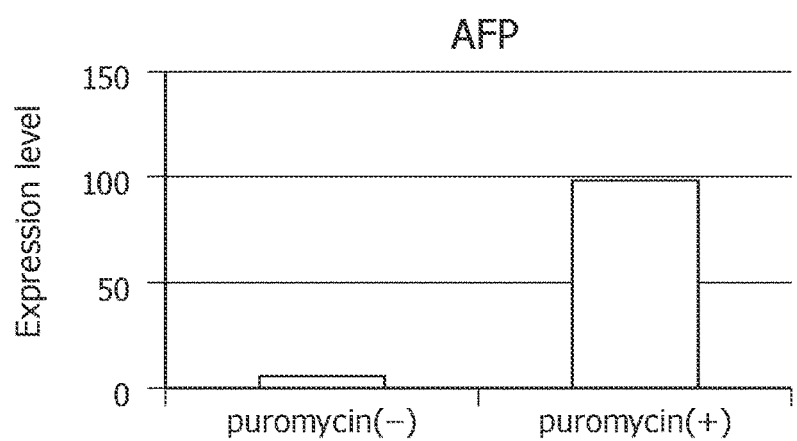
FIGS. 6a-6c are graphs showing results of a qRT-PCR analysis to investigate the expression of hepatic cell markers in cells differentiated from HepaSM cells.
Figure 6B:
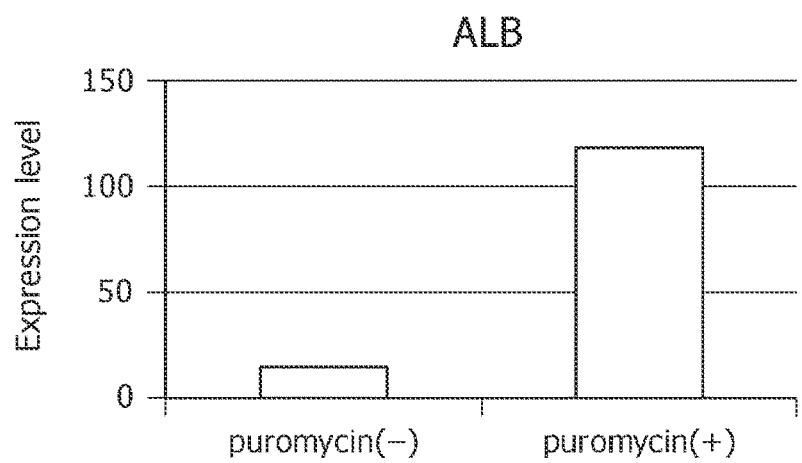
Figure 6C:
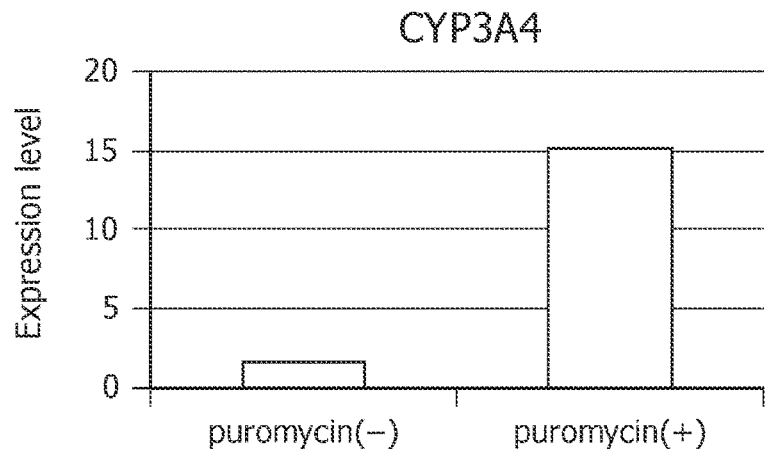

The results are shown in FIGS. 6a-6c. Elevation in all the expression levels of α-fetoprotein (AFP), albumin (ALB) and CYP3A4 was confirmed in the hepatic cells differentiated from the HepaSM cells (puromycin (+)). These results showed that the HepaSM cells can differentiate into hepatic cells expressing CYP3A4 at a high level, i.e., are functional hepatic progenitor cells.

Subsequently, the expression levels of hepatic cell markers in the hepatic cells differentiated from the HepaSM cells were compared with the expression levels of: the hepatic cell markers in HepaRG® cells (obtained from Life Technologies Corp.); hepatic cells obtained by inducing differentiation by the same procedures as in the section 2-2 except that puromycin was not added; and immortalized mature hepatic cells. The expression levels of α-fetoprotein (AFP), albumin (ALB), CYP1A2, CYP2B6 and CYP3A4 in each line of the hepatic cells were quantified by qRT-PCR by the same procedures as described above. The immortalized mature hepatic cells were prepared by isolating and primary culturing hepatic cells according to the procedures described in Alexandrova, K., et al.; Large-Scale Isolation of Human Hepatocytes for Therapeutic Application, Cell Transplantation, 2005; 14 (10): 845-853, and immortalizing the cells by the same procedures as described above.

The results are shown in FIGS. 7a-7e. The hepatic cells differentiated from the HepaSM cells (in the drawing, represented by "puromycin (+)") were confirmed to express α-fetoprotein (AFP), CYP1A2, CYP2B6 and CYP3A4. The hepatic cells differentiated from the HepaSM cells were confirmed to particularly express CYP3A4 at a much higher level than that of the HepaRG® cells (in the drawing, represented by "RG"), the immortalized mature hepatic cells (in the drawing, represented by "MN") or the hepatic cells obtained by inducing differentiation without selection based on puromycin (in the drawing, represented by "YK"). These results showed that the HepaSM cells are stable functional hepatic progenitor cells.

As a result of quantifying the expression levels of hepatic cell markers in the same way as above in hepatic cells differentiated from the HepaNS cells, these hepatic cells were confirmed to express CYP3A4 at a marked high level, as in the hepatic cells differentiated from the HepaSM cells (data not shown). These results showed that the HepaNS cells are also stable functional hepatic progenitor cells.

<4. Induction of Drug Metabolizing Enzyme in Functional Hepatic Progenitor Cells>

The hepatic cells differentiated from the HepaSM cells were subjected to a drug metabolizing enzyme induction test based on the expression of cytochromes P450 (Khuu, D. N. et al.; In Vitro Differentiated Adult Human Liver Progenitor Cells Display Mature Hepatic Metabolic Functions: A Potential Tool for In Vitro Pharmacotoxicological Testing, Cell Transplantation, 2011; 20 (2): 287-302). Rifampicin (solvent: DMSO) was added at 20 μM in terms of a final concentration to modified SCM-6F8 medium, and the cells were cultured therein for 2 days. Then, the expression levels of CYP1A2, CYP2B6 and CYP3A4 were quantified by qRT-PCR by the same procedures as in the section 3. Cells prepared in the same way as above using a medium supplemented with the same amount of DMSO instead of rifampicin (in the drawing, represented by "RFP(−)") were used as a control.

The results are shown in FIGS. 8a-8e. The rifampicin treatment markedly increased the expression levels of all the cytochromes P450 (CYP1A2, CYP2B6 and CYP3A4) in the hepatic cells differentiated from the HepaSM cells (in the drawing, represented by "RFP (+)"). Particularly, the induction of much higher expression of CYP3A4 was confirmed in the hepatic cells differentiated from the HepaSM cells than in the HepaRG® cells (in the drawing, represented by "RG"), the immortalized mature hepatic cells (in the drawing, represented by "MN") or the hepatic cells obtained by inducing differentiation without selection based on puromycin (in the drawing, represented by "YK"). These results showed that the hepatic cells differentiated from the HepaSM cells can be used in a drug toxicity test through in vitro enzyme induction conforming to Drug Interaction Studies-Study Design, Data Analysis, Implications for Dosing, and Labeling Recommendations, 2012 provided by FDA.

As a result of conducting the drug metabolizing enzyme induction test in the same way as above on the hepatic cells differentiated from the HepaNS cells, the induction of markedly high expression of CYP3A4 was confirmed, as in the hepatic cells differentiated from the HepaSM cells (data not shown). These results showed that the hepatic cells differentiated from the HepaNS cells can also be used in the drug toxicity test through in vitro enzyme induction conforming to Drug Interaction Studies-Study Design, Data Analysis, Implications for Dosing, and Labeling Recommendations, 2012 provided by FDA.

<5. Evaluation of Proliferative Capability of Hepatic Cells Differentiated from Functional Hepatic Progenitor Cells>

The hepatic cells differentiated from the HepaSM cells were evaluated for their ability to proliferate on the basis of the expression of proliferating cell markers Ki67 and PCNA. The cells were fixed by paraffin embedding, then deparaffinized, and washed with PBS. Then, 2.5% goat serum/PBS was added thereto, followed by blocking treatment at room temperature for 30 minutes. An anti-Ki67 antibody (DAKO, PC10) or an anti-PCNA antibody (DAKO, MIB-1) (both diluted 1/200) was used as a primary antibody and reacted with the cells at room temperature for 1 hour. Secondary antibody reaction and DAB color development were performed using ImmPRESS Anti-Mouse IgG Kit (Vector Laboratories, Inc.). The cells were washed with water and then subjected to hematoxylin-eosin staining. The obtained specimen was observed under a microscope.

Figure 9A:
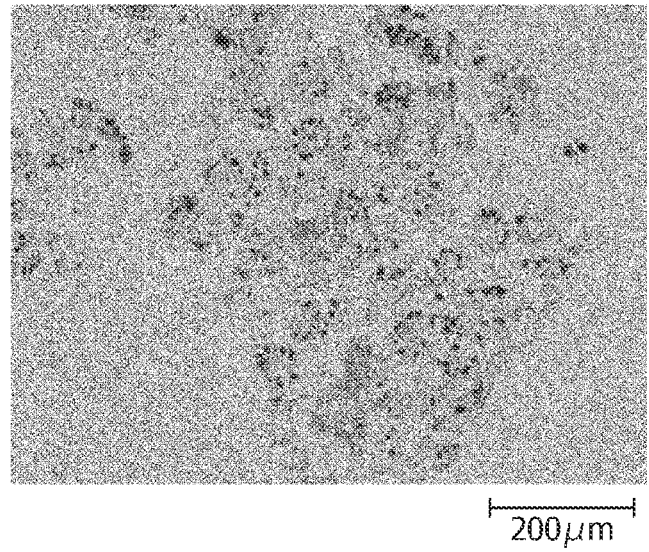
FIGS. 9a-9b are diagrams showing micrographs in which the expression of proliferating cell markers in hepatic cells differentiated from HepaSM cells was confirmed by immunocytochemistry.
Figure 9B:
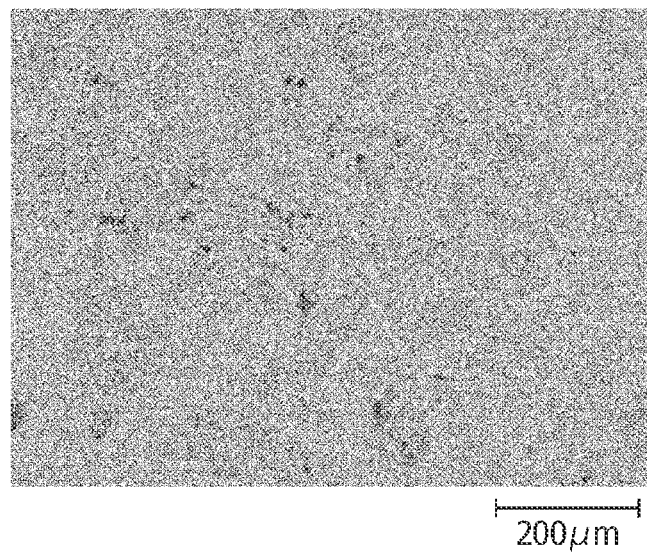
Figure 10A:
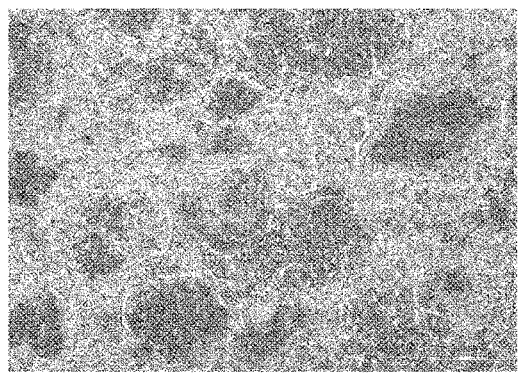
FIGS. 10a-10e are diagrams showing phase-contrast micrographs after treatment with each antibiotic of hepatic progenitor cells differentiated from iPSC-K cells.
Figure 10B:
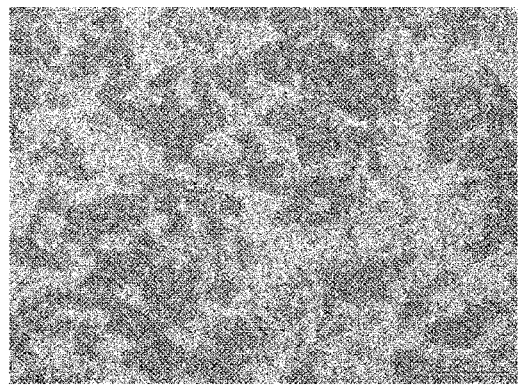
Figure 10C:
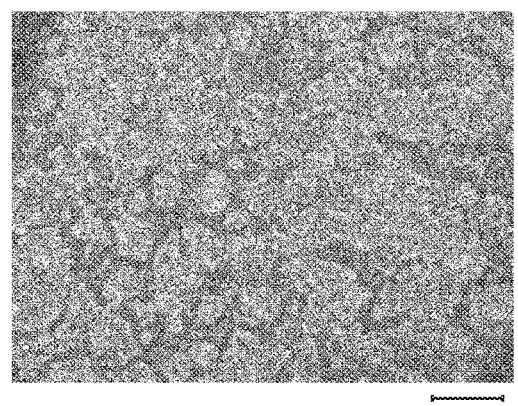
Figure 10D:
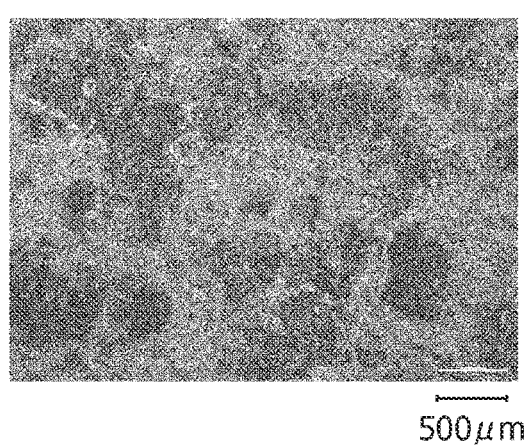
Figure 10E:
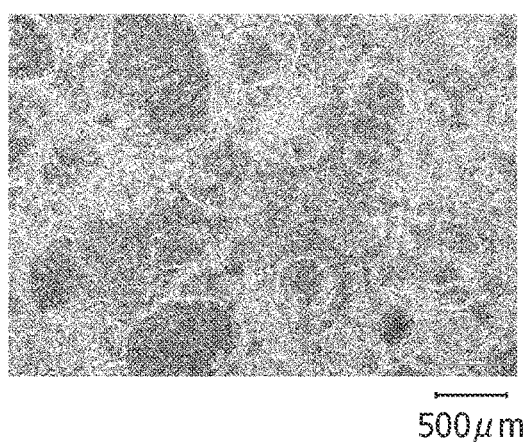
Figure 11A:
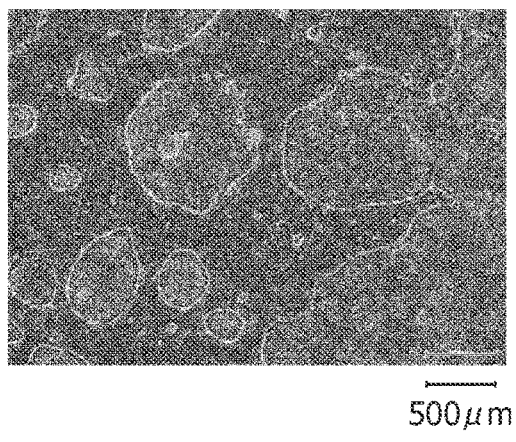
FIGS. 11a-11f are diagrams showing phase-contrast micrographs after treatment with each antibiotic of hepatic progenitor cells differentiated from SEES5 cells.
Figure 11B:
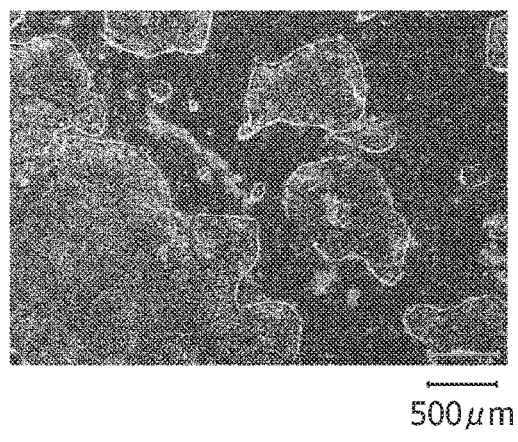
Figure 11C:
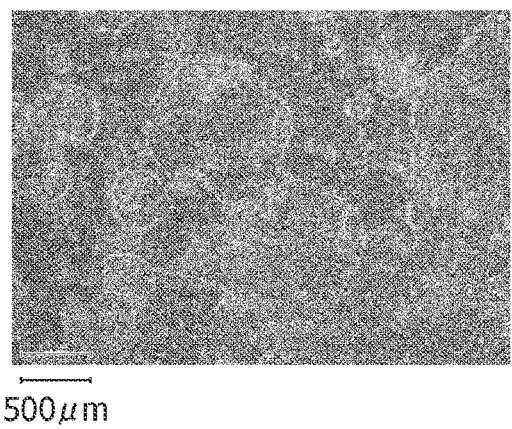
Figure 11D:
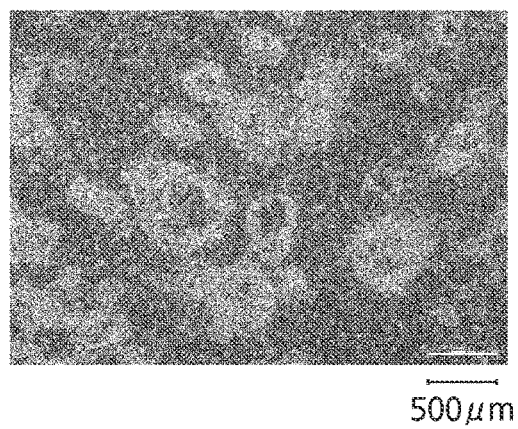
Figure 11E:
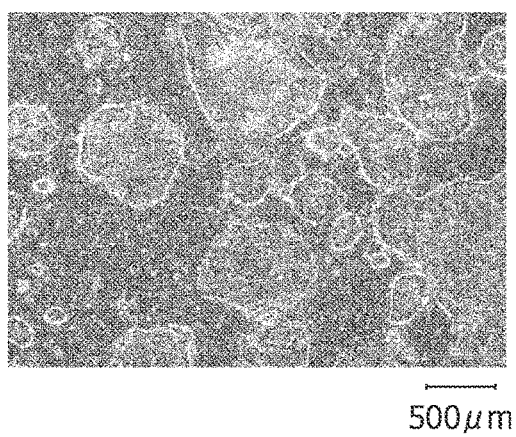
Figure 11F:
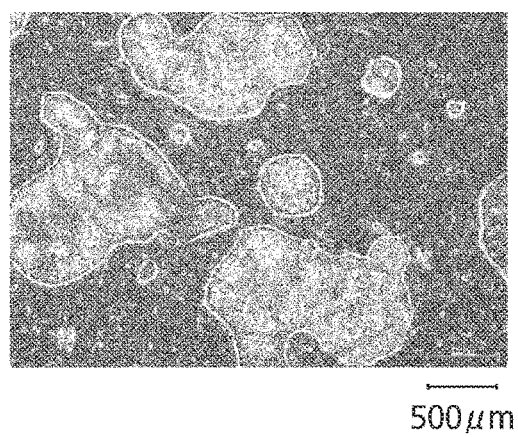

The results are shown in FIGS. 9a-9b. The hepatic cells differentiated from the HepaSM cells were found to express proliferating cell markers PCNA (FIG. 9(a)) and Ki67 (FIG. 9(b)). The hepatic cells differentiated from the HepaNS cells were also confirmed to express the proliferating cell markers Ki67 and PCNA (data not shown). Both the HepaSM cells and the HepaNS cells were confirmed to have high ability to proliferate and to be culturable beyond 6 months.

<6. Preparation of Functional Hepatic Progenitor Cells with Various Antibiotics—(1)>

Functional hepatic progenitor cells were prepared from iPSC-K cells by the same procedures as in the sections (2-1) and (2-2) except that various antibiotics were used instead of puromycin. The antibiotics used and their concentrations, and the number of culture days will be shown below.

Table 5. Antibiotic and Culture Conditions (Preparation of Functional Hepatic Progenitor Cells from iPSC-K Cells)

TABLE 5

| Antibiotic | Product information | Concentration | Culture period |
|---|---|---|---|
| Phleomycin | InvivoGen, ant-ph-1 | 80 μg/ml | 3 days |
| Hygromycin | InvivoGen, ant-hg-1 | 20 μg/ml | 6 days |
| Blasticidin S | InvivoGen, ant-bl-1 | 1 μg/ml | 3 days |
| Zeocin(™) | InvivoGen, ant-zn-l | 600 μg/ml | 6 days |
| G418 | InvivoGen, ant-gn-1 | 300 μg/ml | 3 days |

The results are shown in FIGS. 10a-10e. A colony of the cells was obtained when any of the antibiotics (a) phleomycin, (b) hygromycin, (c) blasticidin S, (d) Zeocin™, and (e) G418 were used.

<7. Preparation of Functional Hepatic Progenitor Cells with Various Antibiotics—(2)>

Functional hepatic progenitor cells were prepared from human ES cells, SEES5 cells (Akutsu, H. et al., Regen. Ther., 2015; 1: 18-29, doi:10.1016/j.reth.2014.12.004), by the following procedures: EBs were formed by the same procedures as in the section (2-1) except that Essential 8 medium (Gibco) was used instead of hiPSC medium. The EBs were recovered and suspended in XF32 medium. The EBs were placed at a concentration of 20 EBs/well in a 24-well plate coated with collagen, and adhesion-cultured at 37° C. for 10 days in 5% $CO_2$. Then, the medium was replaced with HD medium (having the composition of the XF32 medium except for bFGF), and the cells were cultured for 10 days. The medium was further replaced with modified SCM-6F8 medium, and the cells were cultured for 7 days. Then, the medium was replaced with modified SCM-6F8 medium supplemented with each antibiotic. The antibiotics used and their concentrations, and the number of culture days will be shown below.

Table 6. Antibiotic and Culture Conditions (Preparation of Functional Hepatic Progenitor Cells from SEES5 Cells)

TABLE 6

| Antibiotic | Product information | Concentration | Culture period |
|---|---|---|---|
| Phleomycin | InvivoGen, ant-ph-1 | 40 μg/ml | 3 days |
| Hygromycin | InvivoGen, ant-hg-1 | 100 μg/ml | 3 days |
| Blasticidin S | InvivoGen, ant-bl-l | 10 μg/ml | 3 days |
| Zeocin(™) | InvivoGen, ant-zn-1 | 1000 μg/ml | 3 days |

TABLE 6-continued

| Antibiotic | Product information | Concentration | Culture period |
|---|---|---|---|
| G418 | InvivoGen, ant-gn-1 | 200 µg/ml | 3 days |
| Puromycin | Wako, 160-23151 | 5 µg/ml | 3 days |

The results are shown in FIGS. 11a-11f. A colony of the cells was obtained when any of the antibiotics (a) phleomycin, (b) hygromycin, (c) blasticidin S, (d) Zeocin™, (e) G418, and (f) puromycin were used. All of these cells were confirmed to express CYP3A4 at a markedly high level and to be functional hepatic progenitor cells (data not shown).

<8. Preparation of Functional Hepatic Progenitor Cells with Ammonia>

Functional hepatic progenitor cells prepared from iPSC-O cells and selected in the presence of puromycin by the same procedures as in the sections (2-1) and (2-2) except that iPSC-O cells were used instead of iPSC-K cells, and functional hepatic progenitor cells prepared from SEES5 cells and selected in the presence of puromycin in the section 7 were further subjected to selective culture with ammonia by the following procedures. The medium was removed from cultures (10 cm dish) of the functional hepatic progenitor cells prepared from iPSC-O cells or the functional hepatic progenitor cells prepared from SEES5 cells, and the cultures were washed with 5 ml of D-PBS (Gibco). Then, 10 ml of modified SCM-6F8 medium supplemented with 5 mg/ml ammonia or modified SCM-6F8 medium supplemented with 8 mg/ml ammonia was added to the cultures of each cell line, which were then cultured for 2 days under conditions of 37° C. and 5% $CO_2$. Then, the medium was removed, and the cells were washed with 5 ml of D-PBS (Gibco) and supplemented with 10 ml of fresh modified SCM-6F8 medium.

Figure 12A:
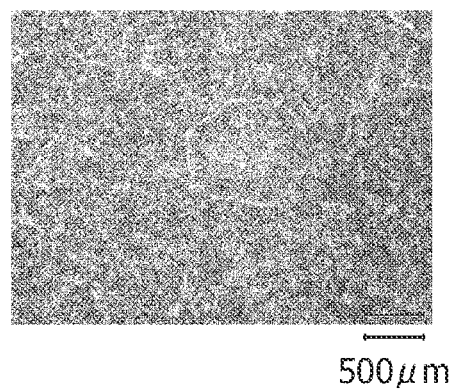
FIGS. 12a-12b are diagrams showing phase-contrast micrographs after puromycin treatment and after ammonia treatment of hepatic progenitor cells differentiated from iPSC-O cells or SEES5 cells.
Figure 12B:
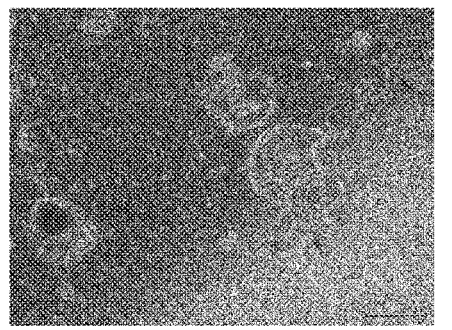
Figure 13A:
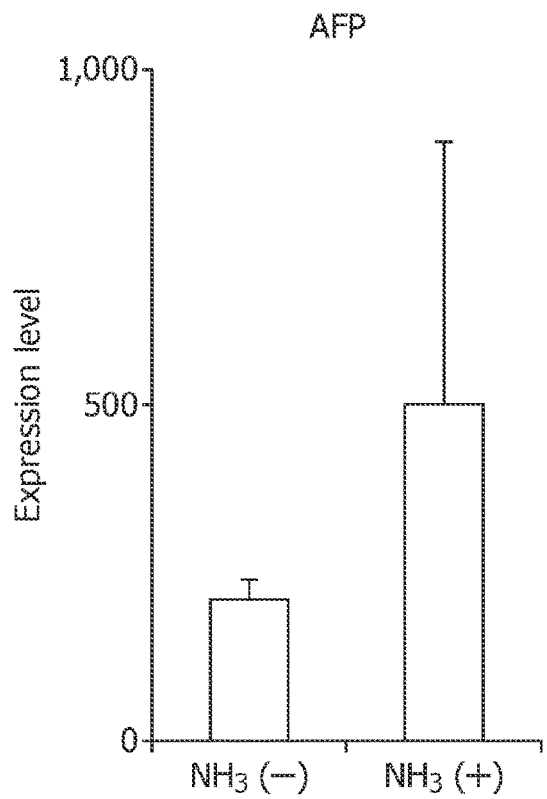
FIGS. 13a-13d are graphs showing results of a qRT-PCR analysis to investigate the expression of metabolizing enzymes in cells obtained by puromycin treatment and ammonia treatment as to hepatic progenitor cells differentiated from iPSC-O cells.
Figure 13B:
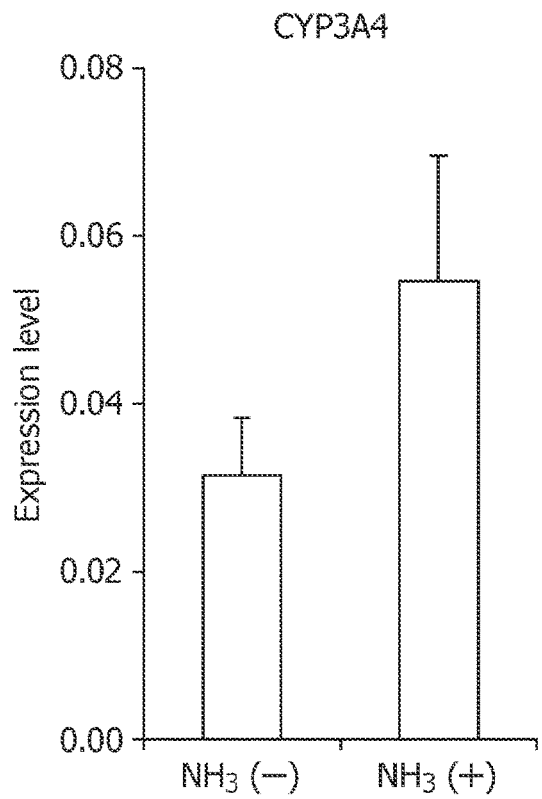
Figure 13C:
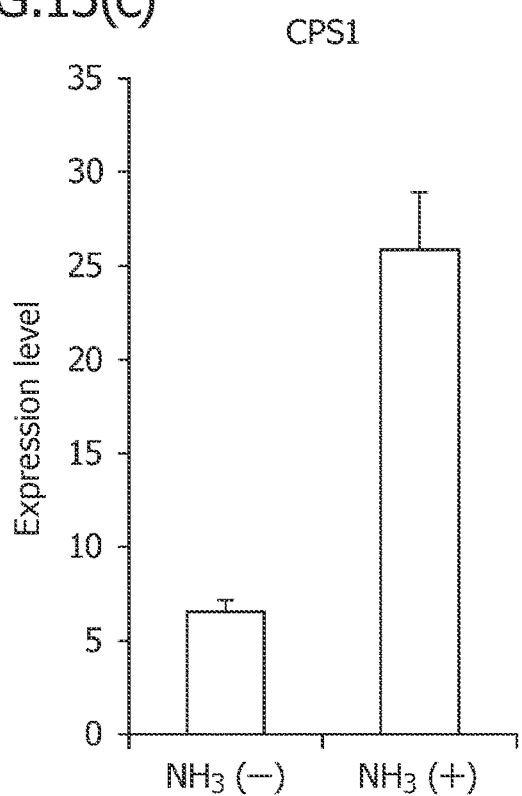
Figure 13D:
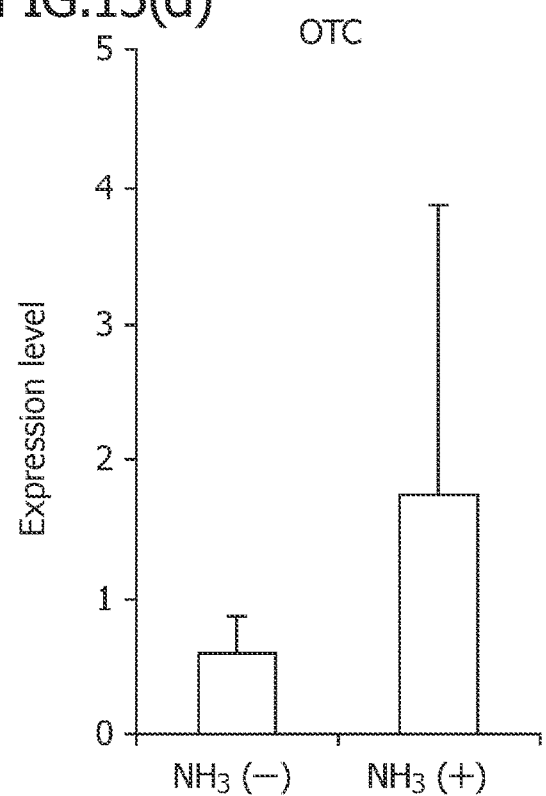

The cultures of the functional hepatic progenitor cells prepared from iPSC-O cells after the selective culture with ammonia are shown in FIG. 12(a), and the cultures of the functional hepatic progenitor cells prepared from SEES5 cells after the selective culture with ammonia are shown in FIG. 12(b). A colony was formed in both the cultures.

Subsequently, the colony of the iPSC-O cell-derived functional hepatic progenitor cells selected in the presence of ammonia was differentiated into hepatic cells by growth culture and culture in modified SCM-6F8 medium for 7 days under conditions of 37° C. and 5% $CO_2$. In the obtained hepatic cells, the expression levels of α-fetoprotein, CYP3A4, carbamyl phosphate synthetase 1 (CPS1), and ornithine transcarbamylase (OTC) were quantified by qRT-PCR by the same procedures as in the section 3. Hepatic cells differentiated from iPSC-O cell-derived functional hepatic progenitor cells subcultured over an equivalent period without selection in the presence of ammonia were used as a control.

Table 7. Primer Set (2) Used in qRT-PCR

TABLE 7

| Gene | Forward and Reverse primers (5'→3') | SEQ NO. |
|---|---|---|
| CPS1 | CAAGTTTTGCAGTGGAATCG | 13 |
|  | GGACAGATGCCTGAGCCTAA | 14 |
| OCT | TTTCCAAGGTTACCAGGTTACAA | 15 |
|  | CTGGGCAAGCAGTGTAAAAAT | 16 |

The results are shown in FIGS. 13a-13d. Elevation in both the expression levels of ammonia metabolizing enzymes CPS1 and OTC was confirmed in the hepatic cells differentiated from the functional hepatic progenitor cells selected in the presence of ammonia ($NH_3$(+)) (FIGS. 13(c) and 13(d)). The selection based on ammonia was also confirmed to further elevate the expression level of CYP3A4 (FIG. 13(b)). These results showed that functional hepatic cells having excellent ability to metabolize drugs and ability to metabolize ammonia can be prepared by selection based on an antibiotic as well as selection based on ammonia.

<9. Preparation of Functional Small Intestinal Epithelial Progenitor Cells>

Gut organoid was prepared from Edom-iPS cells (PLoS Genet., 2011; 7 (5):e1002085, doi.org/10.1371/journal.pgen.1002085), menstrual blood-derived iPS cells, according to the procedures described in Uchida, H. et al., JCI Insight, 2017; 2 (1): e86492. After a lapse of 3 months, the gut organoid was cultured for 2 days in the presence of 2 mg/ml or 400 mg/ml puromycin.

Figure 14A:
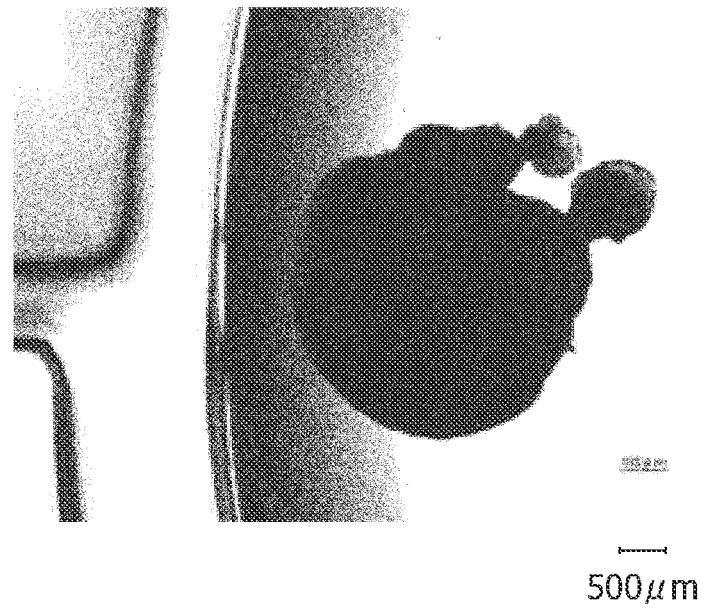
FIGS. 14a-14b are diagrams showing phase-contrast micrographs before puromycin treatment as to gut organoid differentiated from Edom-iPS cells.
Figure 14B:
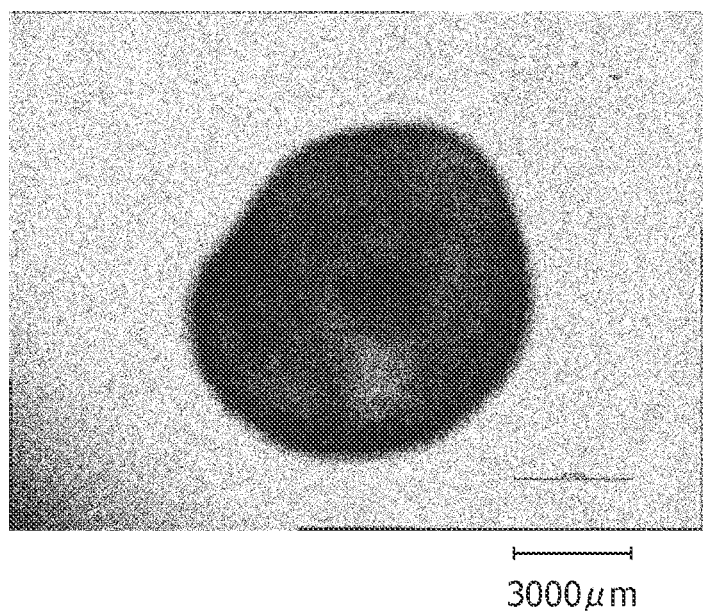
Figure 15A:
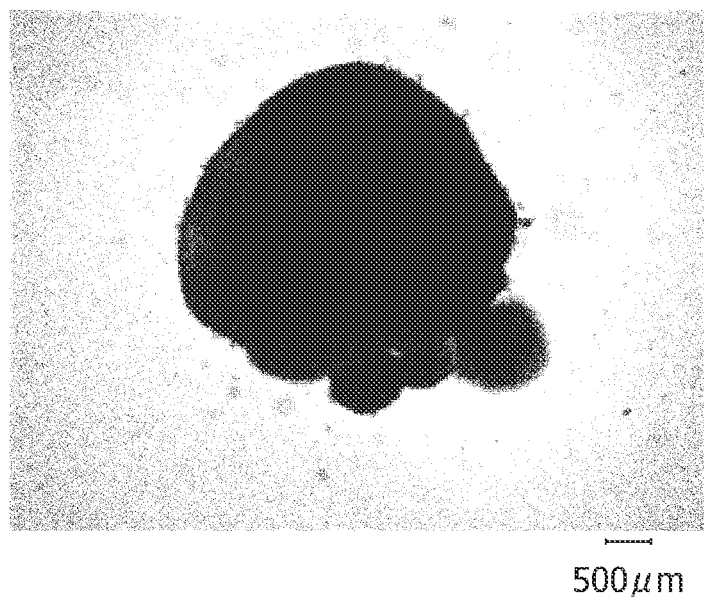
FIGS. 15a-15b are diagrams showing phase-contrast micrographs after puromycin treatment as to gut organoid differentiated from Edom-iPS cells.
Figure 15B:
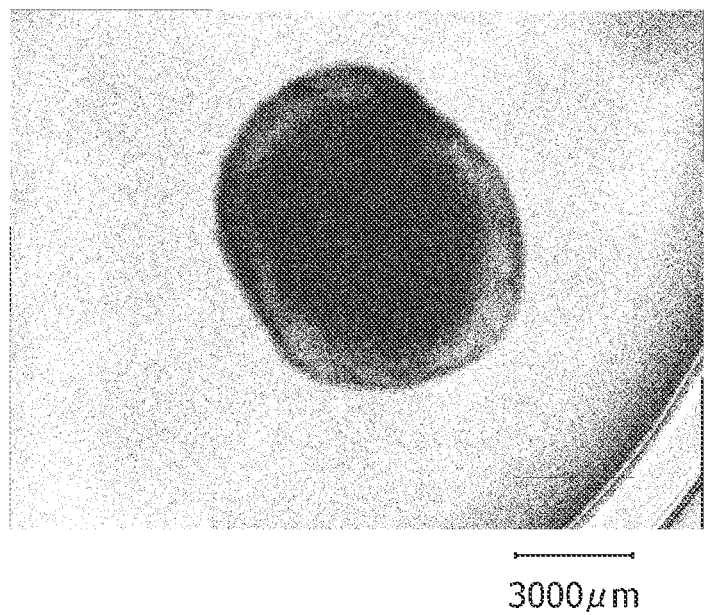

The gut organoid before the puromycin treatment is shown in FIGS. 14a-14b, and the gut organoid after the treatment is shown in FIGS. 15a-15b. Functional small intestinal epithelial progenitor cells having the ability to metabolize drugs were obtained by culture in the presence of 2 mg/ml puromycin (FIG. 15(a)) or 400 mg/ml puromycin (FIG. 15(b)).

The invention claimed is:

1. A method for preparing functional hepatic progenitor cells or functional hepatic cells, or functional small intestinal epithelial progenitor cells or functional small intestinal epithelial cells, the method comprising the step of culturing an isolated cell population comprising hepatic progenitor cells or hepatic cells, or small intestinal epithelial progenitor cells or small intestinal epithelial cells in the presence of 0.1 to 100 µg/ml puromycin and 5 to 15 mg/ml ammonia,
wherein the hepatic progenitor cells or hepatic cells, or the small intestinal epithelial progenitor cells or small intestinal epithelial cells do not comprise an exogenous resistance gene for the antibiotic.

2. The method according to claim 1, wherein the isolated cell population is a primary culture derived from a hepatic tissue or a small intestinal epithelial tissue.

3. The method according to claim 1, wherein the isolated cell population is differentiated from stem cells.

4. The method according to claim 3, wherein the stem cells are embryonic stem (ES) cells.

5. The method according to claim 3, wherein the stem cells are induced pluripotent stem (iPS) cells.

6. The method according to claim 5, wherein the iPS cells are derived from a healthy individual.

7. The method according to claim 5, wherein the iPS cells are derived from a drug-induced liver injury patient or a drug-induced small intestinal injury patient.

8. The method according to claim 1, wherein the culture step is performed in the presence of a hepatic differentiation inducing factor.

9. The method according to claim 8, wherein the hepatic differentiation inducing factor is selected from the group consisting of a cytokine, a cell growth factor, a ROCK inhibitor, a MAPK inhibitor, an ALK inhibitor and an extracellular matrix.

10. A stable functional hepatic progenitor cell line or a stable functional hepatic cell line obtained by a method according to claim 1,
wherein an expression level of CYP3A4 in the functional hepatic progenitor cells is increased by at least 5 times the expression level thereof in a HepaRG cell line, an immortalized mature hepatic cell line, or a hepatic cell line obtained by inducing differentiation without selection based on puromycin.

11. A stable functional small intestinal epithelial progenitor cell line or a stable functional small intestinal epithelial cell line obtained by a method according to claim 1,
wherein an expression level of CYP3A4 in the functional hepatic progenitor cells is increased by at least 5 times the expression level thereof in a HepaRG cell line, an immortalized mature hepatic cell line, or a hepatic cell line obtained by inducing differentiation without selection based on puromycin.

* * * * *

UNITED STATES PATENT AND TRADEMARK OFFICE
CERTIFICATE OF CORRECTION

PATENT NO. : 12,110,507 B2
APPLICATION NO. : 16/958118
DATED : October 8, 2024
INVENTOR(S) : Umezawa et al.

Page 1 of 1

It is certified that error appears in the above-identified patent and that said Letters Patent is hereby corrected as shown below:

In the Specification

Column 19, Line 32: Please correct "$Co_2$" to read --$CO_2$--

Signed and Sealed this
Eleventh Day of February, 2025

Coke Morgan Stewart
*Acting Director of the United States Patent and Trademark Office*